(12) United States Patent
Sapieszko et al.

(10) Patent No.: US 6,325,987 B1
(45) Date of Patent: Dec. 4, 2001

(54) MINERALS AND METHODS FOR THEIR PRODUCTION AND USE

(75) Inventors: Ronald S. Sapieszko, Woodbury, MN (US); Erik M. Erbe, Berwyn, PA (US)

(73) Assignee: Vita Licensing, Inc., Wilmington, DE (US)

( * ) Notice: Subject to any disclaimer, the term of this patent is extended or adjusted under 35 U.S.C. 154(b) by 0 days.

(21) Appl. No.: 09/295,506

(22) Filed: Apr. 21, 1999

Related U.S. Application Data

(62) Division of application No. 08/784,439, filed on Jan. 16, 1997, now Pat. No. 5,939,039.

(51) Int. Cl.[7] .................................................. C01B 25/32
(52) U.S. Cl. ........................ 423/305; 423/311; 424/602
(58) Field of Search .................................. 423/305, 311, 423/314, 315; 424/602, 603

(56) References Cited

U.S. PATENT DOCUMENTS

| | | | |
|---|---|---|---|
| 3,679,360 | 7/1972 | Rubin et al. | 23/109 |
| 4,149,893 | 4/1979 | Aoki et al. | 106/35 |
| 4,612,053 | 9/1986 | Brown et al. | 706/35 |
| 4,673,355 | 6/1987 | Farris et al. | 433/218 |
| 4,711,769 | 12/1987 | Inoue et al. | 423/308 |
| 4,849,193 | 7/1989 | Palmer et al. | 423/308 |
| 4,880,610 | 11/1989 | Constantz | 423/305 |
| 4,891,164 | 1/1990 | Gaffney et al. | 252/629 |
| 4,897,250 | 1/1990 | Sumita | 423/308 |
| 5,034,352 | 7/1991 | Vit et al. | 501/1 |
| 5,047,031 | 9/1991 | Constantz | 606/77 |
| 5,053,212 * | 10/1991 | Constantz et al. | 423/305 |
| 5,129,905 | 7/1992 | Constantz | 606/76 |
| 5,302,362 | 4/1994 | Bedard | 423/306 |
| 5,322,675 | 6/1994 | Hakamatsuka et al. | 423/311 |
| 5,338,334 | 8/1994 | Zhen et al. | 75/362 |
| 5,409,982 | 4/1995 | Imura et al. | 524/417 |
| 5,427,754 | 6/1995 | Nagata et al. | 423/308 |
| 5,496,399 | 3/1996 | Ison et al. | 106/35 |
| 5,522,893 | 6/1996 | Chow et al. | 623/11 |
| 5,525,148 | 6/1996 | Chow et al. | 106/35 |
| 5,545,254 | 8/1996 | Chow et al. | 106/35 |

OTHER PUBLICATIONS

Abbona, F. et al., "Crystallization of calcium and magnesium phosphates from solutions of medium and low concentrations," *Cryst. Res. Technol.*, 1992, 27, 41–48.

Brown, P.W. et al., "Variations in solution chemistry during the low temperature formation of hydroxyapaptite," *J. Am. Ceram. Soc.*, 1991, 74(8), 1848–1854.

Chaair, H. et al., "Precipitation of stoichiometric apatitic tricalcium phosphate prepared by a continuous process," *J. Mater. Chem.*, 1995, 5(6), 895–899.

Driessens, F.C.M. et al., "Effective formulations for the preparation of calcium phosphate bone cements," *J. Mat. Sci.: Mat. Med.*, 1994, 5, 164–170.

Famery, R. et al., "Preparation of alpha–and beta–tricalcium phosphate ceramics, with and without magnesium addition," *Ceram. Int.*, 1994, 20, 327–336.

Fukase, Y. et al., "Setting reactions and compressive strengths of calcium phosphate cements," *J. Dent. Res.*, 1990, 69(12), 1852–1856.

Greenwood, N.N. et al., "Oxoacids of phosphorus and their salts," *Chemistry of the Elements*, Pergamon Press, 1984, 586–595.

Ishikawa, K. et al., "Properties and mechanisms of fast–setting calcium phosphate cements," *J. Mat. Sci.: Mat. Med.*, 1995, 6, 528–533.

Koutsoukos, P. et al., "Crystallization of calcium phosphates. A constant composition study," *J. Am. Chem. Soc.*, 1980, 102, 1553–1557.

Lacout, J.L., "Calcium phosphate as bioceramics," in *Biomaterials—Hard Tissue Repair and Replacement*, Elsevier Science Publishers, 1992, 81–95.

LeGeros, R.Z., "Biodegradation and bioresorption of calcium phospate ceramics," *Clin. Mat.*, 1993, 14(1), 65–88.

LeGeros, R.Z., "Preparation of octacalcium phosphate (OCP): A direct fast method," *Calcif. Tiss. Int.*, 1985, 37, 194–197.

Mirtchi, A. et al., "Calcium phosphate cements: Effect of fluorides on the setting and hardening of beta–tricalcium phosphate—dicalcium phosphate—calcite cements," *Biomat.*, 1991, 12, 505–510.

Monma, H. et al., "Properties of hydroxyapatite prepared by the hydrolysis of tricalcium phosphate," *J. Chem. Tech. Biotechnol.*, 1981, 31, 15–24.

Nancollas, G.H., "The involvement of calcium phosphates in biological mineralization and demineralization processes," *Pure Appl. Chem.*, 1992, 64(11), 1673–1678.

(List continued on next page.)

Primary Examiner—Stuart L. Hendrickson
(74) Attorney, Agent, or Firm—Woodcock Washburn LLP

(57) ABSTRACT

Uniformly sized and shaped particles of metal salts are provided comprised of one or more metal cations in combination with one or more simple oxoacid anions and a general method for the controlled precipitation of said metal salts from aqueous solutions. The methods proceed via the in situ homogeneous production of simple or complex oxoacid anions in which one or more of the nonmetallic elements e.g. Group 5B and 6B (chalcogenides), and 7B (halides) comprising the first oxoacid anion undergo oxidation to generate the precipitant anionic species along with concurrent reduction of the nonmetallic element of a second, dissimilar oxoacid anion. The oxoacid anions are initially present in solution with one or more metal cations known to form insoluble salts with the precipitant anion.

12 Claims, 22 Drawing Sheets

OTHER PUBLICATIONS

Nancollas, G.H., "In vitro studies of calcium phosphate crystallization," in *Biomineralization Chemical and Biochemical Perspectives*, 1989, 157–187.

Nancollas, G.H. et al., "Formation and dissolution mechanisms of calcium phosphates in aqueuos systems," in *Hydroxyapatite and Related Materials*, CRC Press, Inc. 1994, 73–81.

Vereecke G. et al., "Calculation of the solubility diagrams in the system $Ca(OH)_2$—$H_3PO_4$—KOH—$HNO_3$—$CO_2$—$H_2O$," *J. Cryst. Growth*, 1990, 104, 820–832.

Wong, A.T.C. et al., "Prediction of precipitation and transformation behavior of calcium phosphate in aqueous media," in *Hydroxyapatite and Related Materials*, Brown, P.W. et al. (eds.) CRC Press, Inc., 1994, 189–196.

* cited by examiner

MINERALS AND METHODS FOR THEIR PRODUCTION AND USE

CROSS-REFERENCE TO RELATED APPLICATION

This application is a division of Applicant's application Ser. No. 08/784,439, filed Jan. 16, 1997, now U.S. Pat. No. 5,939,039.

FIELD OF THE INVENTION

This invention relates to methods for the preparation of minerals, especially phosphorus containing minerals, to the minerals thus prepared and to methods for their use. In accordance with certain embodiments, minerals are provided which are novel in that they are, at once, substantially homogeneous and non-stoichiometric. They can be produced through novel, low temperature techniques which offer excellent control of composition and morphology.

BACKGROUND OF THE INVENTION

There has been a continuing need for improved methods for the preparation of mineral compositions, especially phosphorus-containing minerals. This long-felt need is reflected in part by the great amount of research found in the pertinent literature. While such interest and need stems from a number of industrial interests, the desire to provide materials which closely mimic mammalian bone for use in repair and replacement of such bone has been a major motivating force. Such minerals are principally calcium phosphate apatites as found in teeth and bones. For example, type-B carbonated hydroxyapatite $[Ca_5(PO_4)_{3-x}(CO_3)_x(OH)]$ is the principal mineral phase found in the body, with variations in protein and organic content determining the ultimate composition, crystal size, morphology, and structure of the body portions formed therefrom.

Calcium phosphate ceramics have been fabricated and implanted in mammals heretofore in many different forms including as shaped bodies, in cements and otherwise. Different stoichiometric compositions such as hydroxyapatite (HAp), tricalcium phosphate (TCP), and tetracalcium phosphate (TTCP), have all been employed to this end in an attempt to match the adaptability, biocompatibility, structure and strength of natural bone. Despite tremendous efforts directed to the preparation of improved calcium phosphate and precursor hydroxyapatite materials for such uses, significant shortcomings still remain.

Early ceramic biomaterials exhibited problems derived from chemical and processing shortcomings that limited stoichiometric control, crystal morphology, surface properties, and, ultimately, reactivity in the body. Intensive milling and comminution of natural minerals of varying composition was required, followed by powder blending and ceramic processing at high temperatures to synthesize new phases for use in vivo.

A number of patents have issued which relate to ceramic biomaterials. Among these are U.S. Pat. No. 4,880,610, B. R. Constantz, "In situ calcium phosphate minerals—method and composition;" U.S. Pat. No. 5,047,031, B. R. Constantz, "In situ calcium phosphate minerals method;" U.S. Pat. No. 5,129,905, B. R. Constantz, "Method for in situ prepared calcium phosphate minerals;" U.S. Pat. No. 4,149,893, H. Aoki, et al, "Orthopaedic and dental implant ceramic composition and process for preparing same;" U.S. Pat. No. 4,612,053, W. E. Brown, et al, "Combinations of sparingly soluble calcium phosphates in slurries and pastes as mineralizers and cements;" U.S. Pat. No. 4,673,355 E. T. Farris, et al, "Solid calcium phosphate materials;" U.S. Pat. No. 4,849,193, J. W. Palmer, et al., "Process of preparing hydroxyapatite;" U.S. Pat. No. 4,897,250, M. Sumita, "Process for producing calcium phosphate;" U.S. Pat. No. 5,322,675, Y. Hakamatsuka, "Method of preparing calcium phosphate;" U.S. Pat. No. 5,338,356, M. Hirano, et al "Calcium phosphate granular cement and method for producing same;" U.S. Pat. No. 5,427,754, F. Nagata, et al., "Method for production of platelike hydroxyapatite;" U.S. Pat. No. 5,496,399, I. C. Ison, et al., "Storage stable calcium phosphate cements;" U.S. Pat. No. 5,522,893, L. C. Chow. et al., "Calcium phosphate hydroxyapatite precursor and methods for making and using same;" U.S. Pat. No. 5,545,254, L. C. Chow, et al., "Calcium phosphate hydroxyapatite precursor and methods for making and using same;" U.S. Pat. No. 3,679,360, B. Rubin, et al., "Process for the preparation of brushite crystals;" U.S. Pat. No. 5,525,148, L. C. Chow, et al., "Self-setting calcium phosphate cements and methods for preparing and using them;" U.S. Pat. No. 5,034,352, J. Vit, et al., "Calcium phosphate materials;" and U.S. Pat. No. 5,409,982, A. Imura, et al "Tetracalcium phosphate-based materials and process for their preparation."

While improvements have been made in ceramic processing technology leading to ceramic biomaterials with better control over starting materials and, ultimately, the final products, improved preparative methods are still greatly desired. Additionally, methods leading to calcium phosphate containing biomaterials which exhibit improved biological properties are also greatly desired despite the great efforts of others to achieve such improvements.

Accordingly, it is a principal object of the present invention to provide improved minerals, especially phosphorus-containing minerals.

A further object of the invention is to provide methods for forming such minerals with improved yields, lower processing temperatures, greater flexibility and control of product formation, and the ability to give rise to minerals having improved uniformity, biological activity, and other properties.

Another object is to improve the yield and control of synthetic mineral formation processes.

Yet another object is to give rise to cement compositions useful in the repair or replacement of bone in orthopaedic and dental procedures.

A further object is to provide minerals which are both substantially uniform and which are non-stoichiometric.

Further objects will become apparent from a review of the present specification.

SUMMARY OF THE INVENTION

The present invention is directed to create new methods for the preparation of minerals, especially phosphorus-containing minerals. The invention also gives rise to uniquely formed minerals, including minerals having improved compositional homogeneity and to minerals having modified crystal structures. New minerals are also provided by the invention, including "non-stoichiometric" minerals, which differ from commonly found minerals, crystal structures which are found in nature, and structures which have traditionally "allowed" ratios of constituent atoms in unit cells.

The new paradigm created by this invention requires a specification of terms used in this invention. The general method starts from raw materials, which are described herein as salts, aqueous solutions of salts, stable hydrosols or other stable dispersions, and/or inorganic acids. The phases produced by the methods of this invention [Redox Precipitation Reaction (RPR) and HYdrothermal PRocessing (HYPR)] are generally intermediate precursor minerals in the physical form of powders, particulates, slurries, and/or pastes. These precursor minerals can be easily converted to a myriad of mixed and pure mineral phases of known and, in some cases, as yet unidentified mineral stoichiometries, generally via a thermal treatment under modest firing conditions compared to known and practiced conventional art.

The methods of the invention are energy efficient, being performed at relatively low temperature, have high yields and are amenable to careful control of product purity, identity and quality. Employment as biological ceramics is a principal use for the materials of the invention, with improved properties being extant. Other uses of the minerals and processes of the invention are also within the spirit of the invention.

DETAILED DESCRIPTION OF PREFERRED EMBODIMENTS

Figure 1:
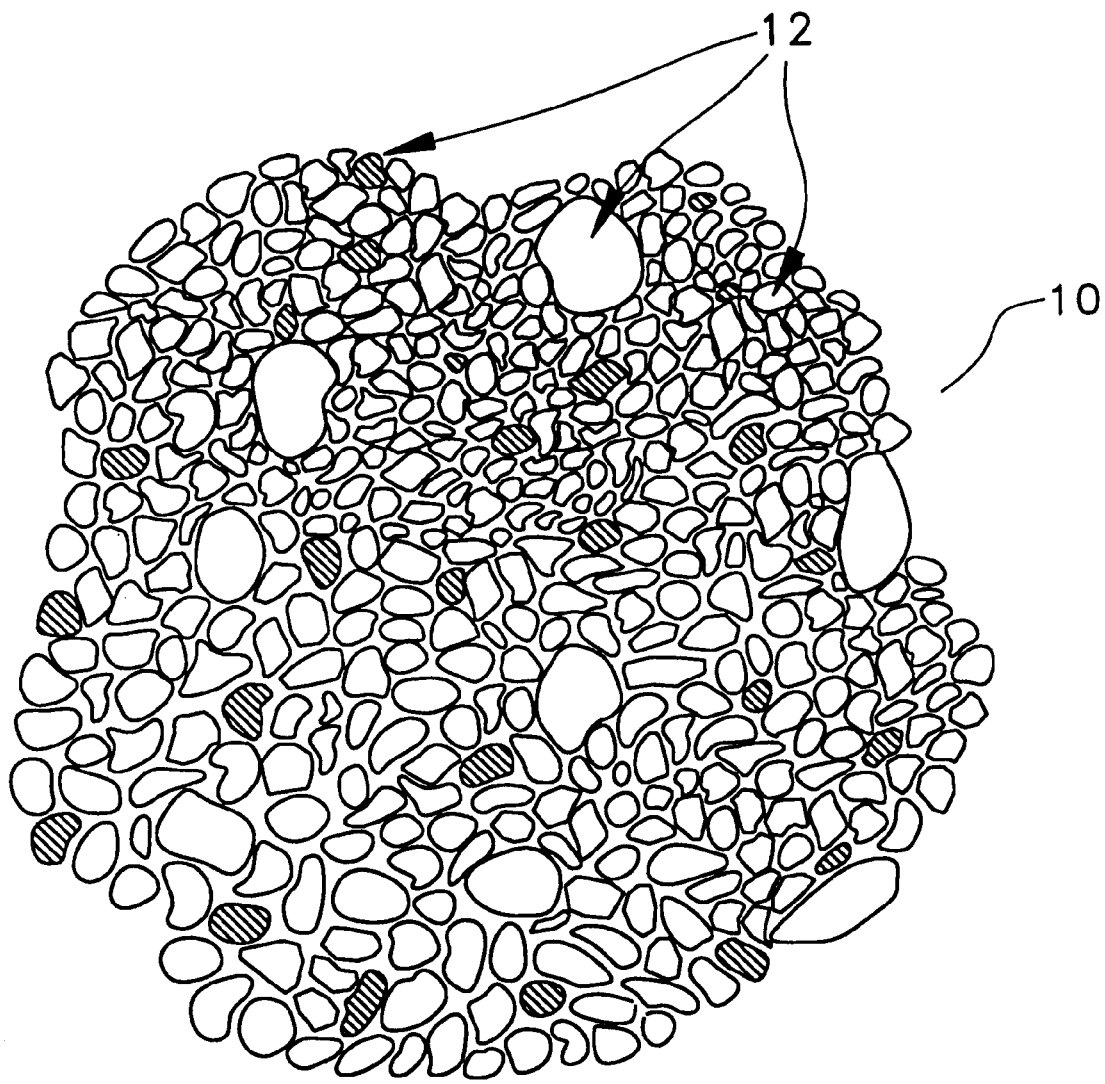
FIG. 1 depicts an aggregated physical structure of an RPR generated, multiphasic β-tricalcium phosphate (β-TCP)+ type-B carbonated apatite (c-HAp) [β-$Ca_3(PO_4)_2$+$Ca_5$ $(PO_4)_{3-x}(CO_3)_x(OH)$] prepared in accordance with one embodiment this invention. The entire agglomerated particle is approximately 10 μm, and the individual crystallites are typically less than about 1 μm and relatively uniform in particle size and shape.

In accordance with the present invention, methods are provided for preparing an intermediate precursor mineral of at least one metal cation and at least one oxoanion. These methods comprise preparing an aqueous solution of the metal cation and at least one oxidizing agent. The solution is augmented with at least one soluble precursor anion oxidizable by said oxidizing agent to give rise to the precipitant oxoanion. The oxidation-reduction reaction thus contemplated is conventionally initiated by heating the solution under conditions of temperature and pressure effective to give rise to said initiation. In accordance with preferred embodiments of the invention, the oxidation-reduction reaction causes at least one gaseous product to evolve and the desired intermediate precursor mineral to precipitate from the solution.

The intermediate precursor mineral thus prepared can be treated in a number of ways. Thus, it may be heat treated in accordance with one or more paradigms to give rise to a preselected crystal structure or other preselected morphological structures therein.

In accordance with preferred embodiments, the oxidizing agent is nitrate ion and the gaseous product is a nitrogen oxide, generically depicted as $NO_{x(g)}$. It is preferred that the precursor mineral provided by the present methods be substantially homogeneous. It is also preferred that the temperature reached by the oxidation-reduction reaction not exceed about 150° C. unless the reaction is run under hydrothermal conditions or in a pressure vessel.

In accordance with other preferred embodiments, the intermediate precursor mineral provided by the present invention is a calcium phosphate. It is preferred that such mineral precursor comprise, in major proportion, a solid phase which cannot be identified singularly with any conventional crystalline form of calcium phosphate. At the same time, the calcium phosphate mineral precursors of the present invention are substantially homogeneous and do not comprise a physical admixture of naturally occurring or conventional crystal phases.

In accordance with preferred embodiments, the low temperature processes of the invention lead to the homogeneous precipitation of high purity powders from highly concentrated solutions. Subsequent modest heat treatments convert the intermediate material to e.g. novel monophasic calcium phosphate minerals or novel biphasic β-tricalcium phosphate (β-TCP)+type-B, carbonated apatite (c-HAp) [β-$Ca_3$($PO_4$)$_2$+$Ca_5$($PO_4$)$_{3-x}$($CO_3$)$_x$(OH)] particulates.

In other preferred embodiments, calcium phosphate salts are provided through methods where at least one of the precursor anions is a phosphorus oxoanion, preferably introduced as hypophosphorus acid or a soluble alkali or alkaline-earth hypophosphite salt. For the preparation of such calcium phosphates, it is preferred that the initial pH be maintained below about 3, and still more preferably below about 1.

The intermediate precursor minerals prepared in accordance with the present methods are, themselves, novel and not to be expected from prior methodologies. Thus, such precursor minerals can be, at once, non-stoichiometric and possessed of uniform morphology.

It is preferred in connection with some embodiments of the present invention that the intermediate precursor minerals produced in accordance with the present methods be heated, or otherwise treated, to change their properties. Thus, such materials may be heated to temperatures as low as 300° C. up to about 700° C. to give rise to certain beneficial transformations. Such heating will remove extraneous materials from the mineral precursor, will alter its composition and morphology in some cases, and can confer upon the mineral a particularized and preselected crystalline structure. Such heat treatment is to temperatures which are considerably less than are conventionally used in accordance with prior methodologies used to produce the end product mineral phases. Accordingly, the heat treatments of the present invention do not, of necessity, give rise to the common crystalline morphologies structures of monetite, dicalcium or tricalcium phosphate, tetracalcium phosphate, etc., but, rather, to new and unobvious morphologies which have great utility in the practice of the present invention.

In accordance with the present invention, the minerals formed hereby are useful in a wide variety of industrial, medical, and other fields. Thus, calcium phosphate minerals produced in accordance with preferred embodiments of the present invention may be used in dental and orthopaedic surgery for the restoration of bone, tooth material and the like. The present minerals may also be used as precursors in chemical and ceramic processing, and in a number of industrial methodologies, such as crystal growth, ceramic processing, glass making, catalysis, bioseparations, pharmaceutical excipients, gem synthesis, and a host of other uses. Uniform microstructures of unique compositions of minerals produced in accordance with the present invention confer upon such minerals wide utility and great "value added."

Improved precursors provided by this invention yield lower temperatures of formation, accelerated phase transition kinetics, greater compositional control, homogeneity, and flexibility when used in chemical and ceramic processes. Additionally, these chemically-derived, ceramic precursors have fine crystal size and uniform morphology with subsequent potential for more closely resembling or mimicking natural structures found in the body.

Controlled precipitation of specific phases from aqueous solutions containing metal cations and phosphate anions represents a difficult technical challenge. For systems containing calcium and phosphate ions, the situation is further complicated by the multiplicity of phases that may be involved in the crystallization reactions as well as by the facile phase transformations that may proceed during mineralization. The solution chemistry in aqueous systems containing calcium and phosphate species has been scrupulously investigated as a function of pH, temperature, concentration, anion character, precipitation rate, digestion time, etc. (P. Koutsoukos, Z. Amjad, M. B. Tomson, and G. H. Nancollas, "Crystallization of calcium phosphates. A constant composition study," J. Am. Chem. Soc. 102: 1553 (1980); A. T. C. Wong and J. T. Czernuszka, "Prediction of precipitation and transformation behavior of calcium phosphate in aqueous media," in Hydroxyapatite and Related Materials, pp 189–196 (1994), CRC Press, Inc.; G. H. Nancollas, "In vitro studies of calcium phosphate crystallization," in Biomineralization—Chemical and Biochemical Perspectives, pp 157–187 (1989)).

Solubility product considerations impose severe limitations on the solution chemistry. Furthermore, methods for generating specific calcium phosphate phases have been described in many technical articles and patents (R. Z. LeGeros, "Preparation of octacalcium phosphate (OCP): A direct fast method," Calcif. Tiss. Int. 37: 194 (1985)). As discussed above, none of this aforementioned art employs the present invention.

Several sparingly soluble calcium phosphate crystalline phases, so called "basic" calcium phosphates, have been characterized, including alpha- and beta-tricalcium phosphate ($\alpha$-TCP, $\beta$-TCP, $Ca_3(PO_4)_2$), tetracalcium phosphate (TTCP,$Ca_4(PO_4)_2O$), octacalcium phosphate (OCP, $Ca_4H$ $(PO_4)_3.-nH_2O$, where 2<n<3), and calcium hydroxyapatite (HAp, $Ca_5(PO_4)_3(OH)$). Soluble calcium phosphate phases, so called "acidic" calcium phosphate crystalline phases, include dicalcium phosphate dihydrate (brushite-DCPD, $CaHPO_4.H_2O$), dicalcium phosphate anhydrous (monetite-DCPA, $CaHPO_4$), monocalcium phosphate monohydrate (MCPM, $Ca(H_2PO_4)_2$—$H_2O$), and monocalcium phosphate anhydrous (MCPA, $Ca(H_2PO_4)_2$). These calcium phosphate compounds are of critical importance in the area of bone cements and bone grafting materials. The use of DCPD, DCPA, $\alpha$-TCP, $\beta$-TCP, TTCP, OCP, and HAp, alone or in combination, has been well documented as biocompatible coatings, fillers, cements, and bone-forming substances (F. C. M. Driessens, M. G. Boltong, O. Bermudez, J. A. Planell, M. P. Ginebra, and E. Fernandez, "Effective formulations for the preparation of calcium phosphate bone cements," J. Mat. Sci.: Mat. Med. 5: 164 (1994); R. Z. LeGeros, "Biodegradation and bioresorption of calcium phosphate ceramics," Clin. Mat. 14(1): 65 (1993); K. Ishikawa, S. Takagi, L. C. Chow, and Y. Ishikawa, "Properties and mechanisms of fast-setting calcium phosphate cements," J. Mat. Sci.: Mat. Med. 6: 528 (1995); A. A. Mirtchi, J. Lemaitre, and E. Munting, "Calcium phosphate cements: Effect of fluorides on the setting and hardening of beta-tricalcium phosphate—dicalcium phosphate—calcite cements," Biomat. 12: 505 (1991); J. L. Lacout, "Calcium phosphate as bioceramics," in Biomaterials—Hard Tissue Repair and Replacement, pp 81–95 (1992), Elsevier Science Publishers).

Generally, these phases are obtained via thermal or hydrothermal conversion of (a) solution-derived precursor calcium phosphate materials, (b) physical blends of calcium salts, or (c) natural coral. Thermal transformation of synthetic calcium phosphate precursor compounds to TCP or TTCP is achieved via traditional ceramic processing regimens at high temperature, greater than about 800° C. Thus, despite the various synthetic pathways for producing calcium phosphate precursors, the "basic" calcium phosphate materials used in the art have generally all been subjected to a high temperature treatment, often for extensive periods of time. For the preparation of other "basic" calcium phosphate materials according to this invention, see also H. Monma, S. Ueno, and T. Kanazawa, "Properties of hydroxyapatite prepared by the hydrolysis of tricalcium phosphate," J. Chem. Tech. Biotechnol. 31: 15 (1981); H. Chaair, J. C. Heughebaert, and M. Heughebaert, "Precipitation of stoichiometric apatitic tricalcium phosphate prepared by a continuous process," J. Mater. Chem. 5(6): 895 (1995); R. Famery, N. Richard, and P. Boch, "Preparation of alpha- and beta-tricalcium phosphate ceramics, with and without magnesium addition," Ceram. Int. 20: 327 (1994); Y. Fukase, E. D. Eanes, S. Takagi, L. C. Chow, and W. E. Brown, "Setting reactions and compressive strengths of calcium phosphate cements," J. Dent. Res. 69(12): 1852 (1990).

The present invention represents a significant departure from prior methods for synthesizing metal phosphate minerals in general, and calcium phosphate powders in particular, in that the materials are precipitated from homogeneous solution using a novel Redox Precipitation Reaction (RPR). They can be subsequently converted to TCP, HAp and/or combinations thereof at modest temperatures and short firing schedules. Furthermore, precipitation from homogeneous solution (PFHS) in accordance with this invention, has been found to be a means of producing particulates of uniform size and composition in a form heretofore not observed in the prior art.

The use of hypophosphite [$H_2PO_2^-$] anion as a precursor to phosphate ion generation has been found to be preferred since it circumvents many of the solubility constraints imposed by conventional calcium phosphate precipitation chemistry and, furthermore, it allows for uniform precipitation at high solids levels. For example, reactions can be performed in accordance with the invention giving rise to product slurries having in excess of 30% solids. Nitrate anion is the preferred oxidant although other oxidizing agents are also useful.

The novel use of nitrate anion under strongly acidic conditions as the oxidant for the hypophosphite to phosphate reaction is beneficial from several viewpoints. Nitrate is a readily available and an inexpensive oxidant. It passivates stainless steel (type 316 SS) and is non-reactive to glass processing equipment. Its oxidation byproducts ($NO_x$) are manageable via well-known pollution control technologies, and any residual nitrate will be fugitive, as $NO_x$ under the thermal conversion schedule to which the materials are usually subjected, thus leading to exceedingly pure final materials.

Use of reagent grade metal nitrate salts and hypophosphorus acid, as practiced in this invention, will lead to metal phosphate phases of great purity.

Methods for producing useful calcium phosphate-based materials are achieved by reduction-oxidation precipitation reactions (RPR) generally conducted at ambient pressure and relatively low temperatures, usually below 250° C. and preferably below 200° C., most preferably below 150° C. The manner of initiating such reactions is determined by the starting raw materials, their treatment, and the redox electrochemical interactions among them.

The driving force for the RPR is the concurrent reduction and oxidation of anionic species derived from solution precursors. Advantages of the starting solutions can be realized by the high initial concentrations of ionic species, especially calcium and phosphorus species. It has been found that the use of reduced phosphorus compounds leads to solution stability at ionic concentrations considerably greater than if fully oxidized [$PO_4$]$^{-3}$ species were used. Conventional processing art uses fully oxidized phosphorus oxoanion compounds and is, consequently, hindered by pH, solubility, and reaction temperature constraints imposed by the phosphate anion.

Typical reducible species are preferably nitric acid, nitrate salts (e.g. $Ca(NO_3)_2.4H_2O$), or any other reducible nitrate compound, which is highly soluble in water. Other reducible species include nitrous acid ($HNO_2$) or nitrite ($NO2^-$) salts.

Among the oxidizable species which can be used are hypophosphorus acid or hypophosphite salts (e.g. Ca ($H_2PO_2$)$_2$) which are highly soluble in water. Other oxidizable species which find utility include acids or salts of phosphites ($HPO_3^{2-}$), pyrophosphites ($H_2P_2O_5^{2-}$), thiosulfate ($S_2O_3^{2-}$), tetrathionate ($S_4O_6^{2--}$), dithionate ($S_2O_4^{2-}$) trithionate ($S_3O_6^{2-}$), sulfite ($SO_3^{2-}$), and dithionate ($S_2O_6^{2-}$). In consideration of the complex inorganic chemistry of the oxoanions of Groups 5B, 6B, and 7B elements, it is anticipated that other examples of oxidizable anions can be utilized in the spirit of this invention.

The cation introduced into the reaction mixture with either or both of the oxidizing or reducing agents are preferably oxidatively stable (i.e. in their highest oxidation state). However, in certain preparations, or to effect certain reactions, the cations may be introduced in a partially reduced oxidation state. Under these circumstances, adjustment in the amount of the oxidant will be necessary in order to compensate for the electrons liberated during the oxidation of the cations during RPR.

It is well known in the art that for solutions in equilibrium with ionic precipitates, the solute concentrations of the reactant ions are dictated by solubility product relationships and supersaturation limitations. For the $Ca^{2+}$—$[PO_4]^{-3}$ system, these expressions are exceedingly complicated, due in large part to the numerous pathways (i.e., solid phases) for relieving the supersaturation conditions. Temperature, pH, ionic strength, ion pair formation, the presence of extraneous cations and anions all can affect the various solute species equilibria and attainable or sustainable supersaturation levels ( F. Abbona, M. Franchini-Angela, and R. Boistelle, "Crystallization of calcium and magnesium phosphates from solutions of medium and low concentrations," Cryst. Res. Technol. 27: 41 (1992); G. H. Nancollas, "The involvement of calcium phosphates in biological mineralization and demineralization processes," Pure Appl. Chem. 64(11): 1673 (1992); G. H. Nancollas and J. Zhang, "Formation and dissolution mechanisms of calcium phosphates in aqueous systems," in Hydroxyapatite and Related Materials, pp 73–81 (1994), CRC Press, Inc.; P. W. Brown, N. Hocker, and S. Hoyle, "Variations in solution chemistry during the low temperature formation of hydroxyapatite," J. Am. Ceram. Soc. 74(8): 1848 (1991); G. Vereecke and J. Lemaitre, "Calculation of the solubility diagrams in the system $Ca(OH)_2$—$H_3PO_4$—KOH—$HNO_3$—$CO_2$—$H_2O$," J. Cryst. Growth 104: 820 (1990); A. T. C. Wong and J. T. Czernuszka, "Prediction of precipitation and transformation behavior of calcium phosphate in aqueous media," in Hydroxyapatite and Related Materials, pp 189–196 (1994), CRC Press, Inc.; G. H. Nancollas, "In vitro studies of calcium phosphate crystallization," in Biomineralization—Chemical and Biochemical Perspectives, pp 157–187 (1989)).

Additionally, while thermodynamics will determine whether a particular reaction is possible, kinetic effects may be very much more important in explaining the absence or presence of particular calcium phosphate phases during precipitation reactions.

In the practice of certain preferred embodiments of this invention to give rise to calcium phosphates, soluble calcium ion is maintained at concentrations of several molar in the presence of soluble hypophosphite anion which is, itself, also at high molar concentrations. The solution is also at a very low pH due to the presence of nitric and hypophosphorus acids. Indeed, such solutions of calcium and hypophosphite ions can be stable indefinitely, with respect to precipitation, at room temperature or below. In contrast, it is impossible (in the absence of ion complexation or chelating agents) to simultaneously maintain calcium ions and phosphate anions at similar concentrations as a solid phase would immediately precipitate to relieve the supersaturation. Upon oxidation of the hypophosphite ion to phosphite and, subsequently, to phosphate, calcium phosphate phases are rapidly precipitated from homogeneous solution under solution conditions unique (concentration, pH, ionic strength) for the formation of such materials. The combination of homogeneous generation of precipitating anion, rapid precipitation kinetics, and unique thermodynamic regime results in the formation of calcium phosphate precursors having unique size and morphological characteristics, surface properties, and reactivities.

The foregoing consideration will also apply to minerals other than the calcium phosphates. Per force, however, the phase diagram, equilibrium condition and constituent mineral phases will differ in each family of minerals.

Uniformly sized and shaped particles of metal salts comprised of one or more metal cations in combination with one or more oxoacid anions can result from the present general method for the controlled precipitation of said metal salts from aqueous solutions. These proceed via the in situ homogeneous production of simple or complex oxoacid anions of one or more of the nonmetallic elements, Group 5B and 6B (chalcogenides), and 7B (halides). The first oxoacid anion undergoes oxidation (increase in chemical oxidation state) to generate the precipitant anionic species along with concurrent reduction (decrease in chemical oxidation state) of the nonmetallic element of a second, dissimilar oxoacid anion, all oxoacid anions initially being present in solution with one or more metal cations known to form insoluble salts with the precipitant anion. The metal cations are, preferably, oxidatively stable, but may, undergo oxidation state changes themselves under certain conditions.

RPR is induced preferably by heating a homogeneous solution, so as to promote the onset and continuation of an exothermic redox reaction. This exothermic reaction results in the generation of gases, usually various nitrogen oxide gases such as $NO_x$, where $0.5<x<2$, as the soluble reduced phosphorus species are converted to precipitating anions which then homogeneously precipitate the calcium ions from the reaction medium. At this stage, the reaction is essentially complete, resulting in an assemblage of ultrafine precipitated particles of the predetermined calcium-phosphate stoichiometry. The reaction yield is high as is the purity of the reaction products.

Figure 2:
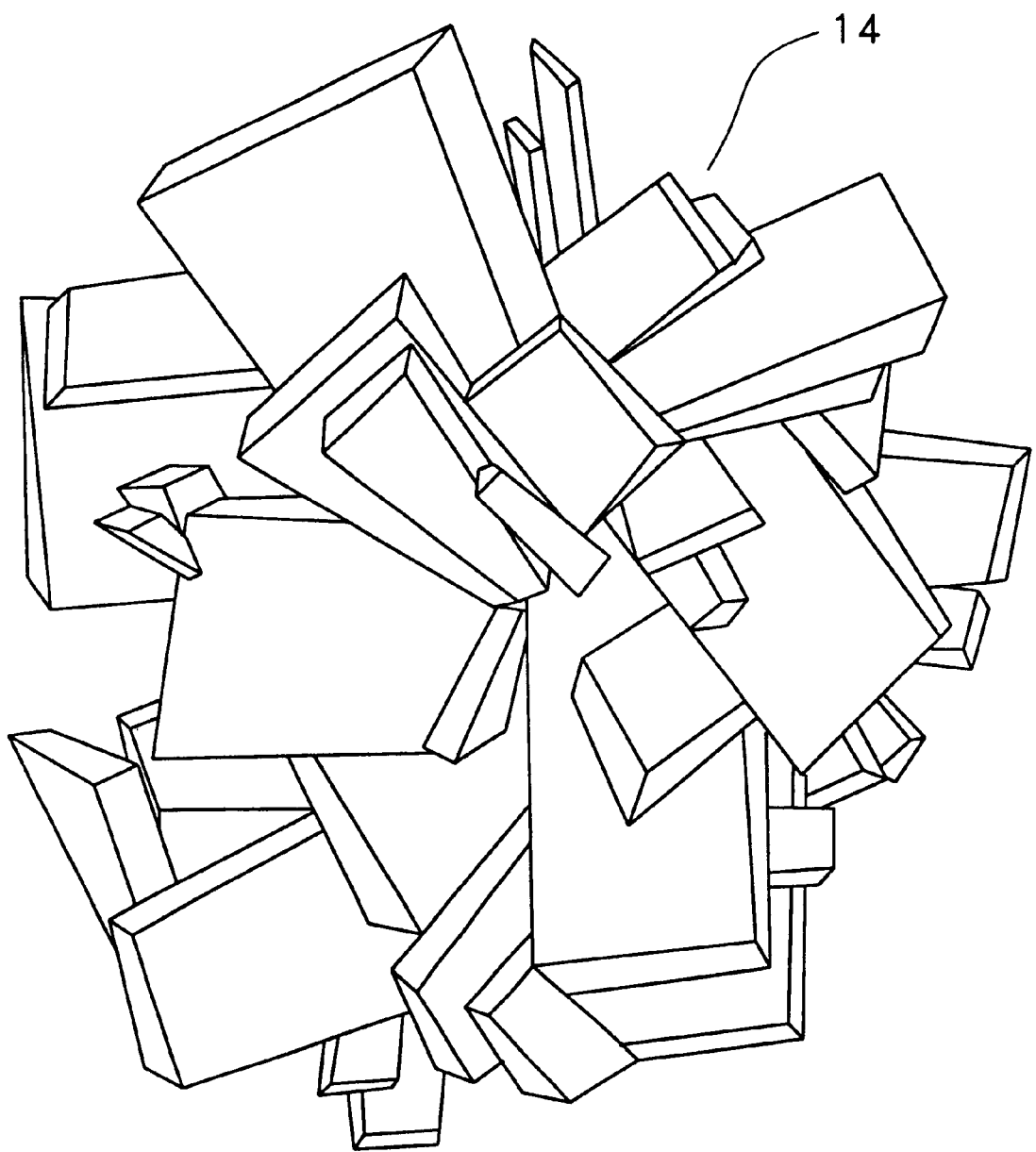
FIG. 2 represents assembled monetite, $CaHPO_4$ particles formed from a hydrothermal precipitation in accordance with this invention. The entire particle assemblage is typically about 30 μm and is comprised of relatively uniformly rectangular cubes and plate-like crystallites of various sizes and aspect ratios.
Figure 3:
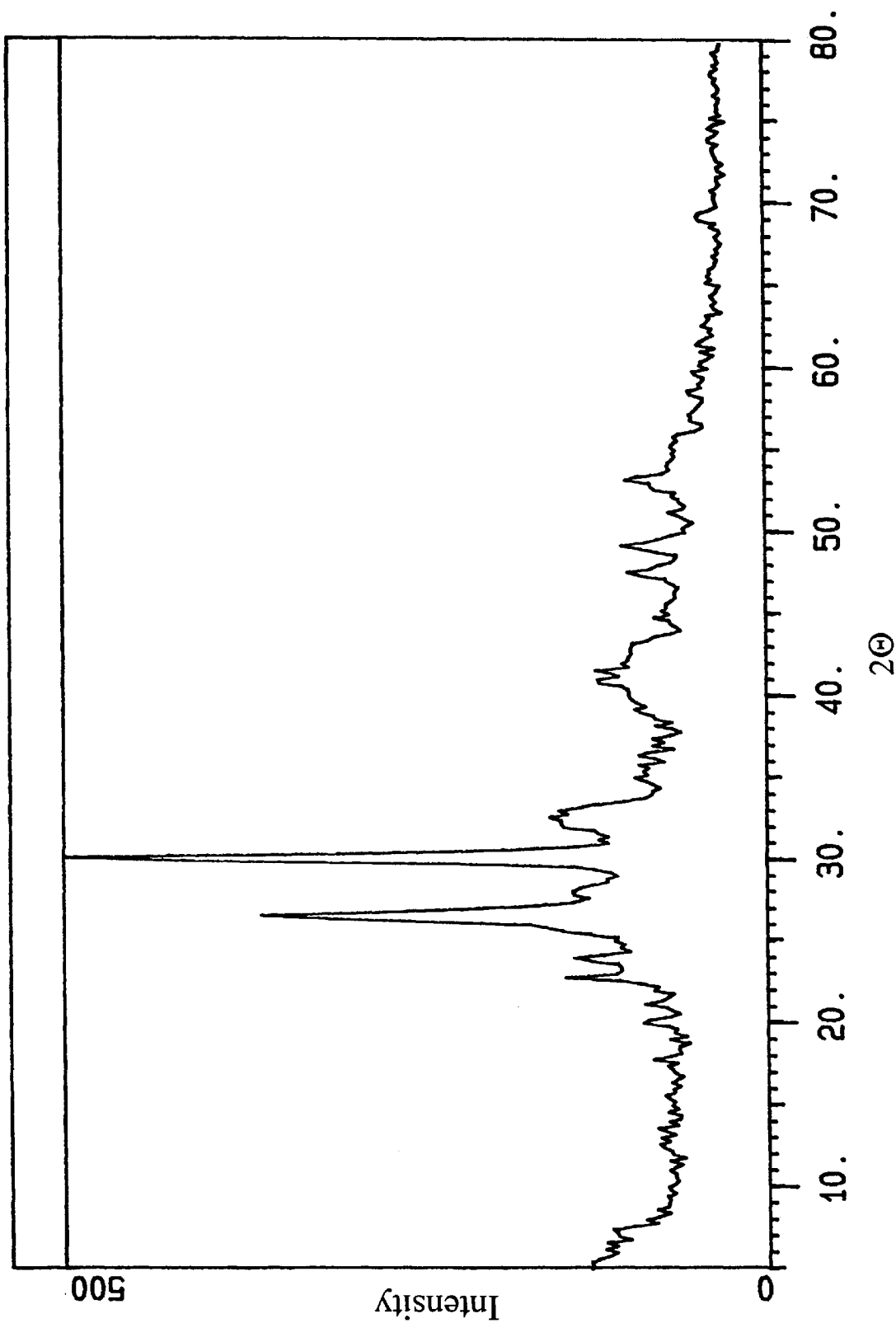
FIG. 3 is an X-ray Diffraction (XRD) plot of RPR generated calcium phosphate precursor mineral heated to 100° C. for 1 hour. The peak position and relative intensities indicate the presence of the crystal phase monetite.
Figure 4:
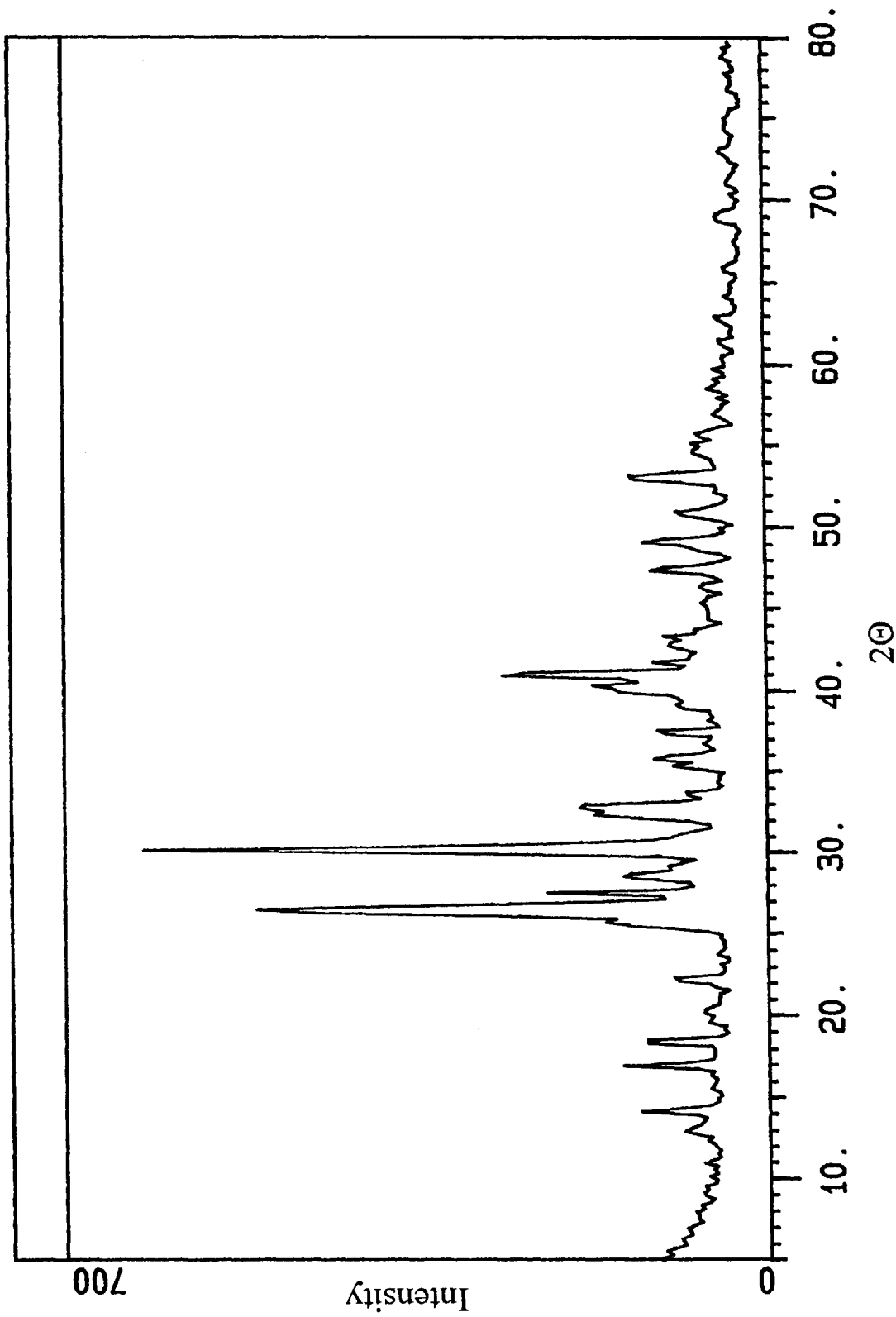
FIG. 4 is an X-ray Diffraction (XRD) plot of an RPR generated calcium phosphate precursor mineral heated to 300° C. for 1 hour. The peak position and relative intensities indicate the presence of the crystal phase monetite.
Figure 5:
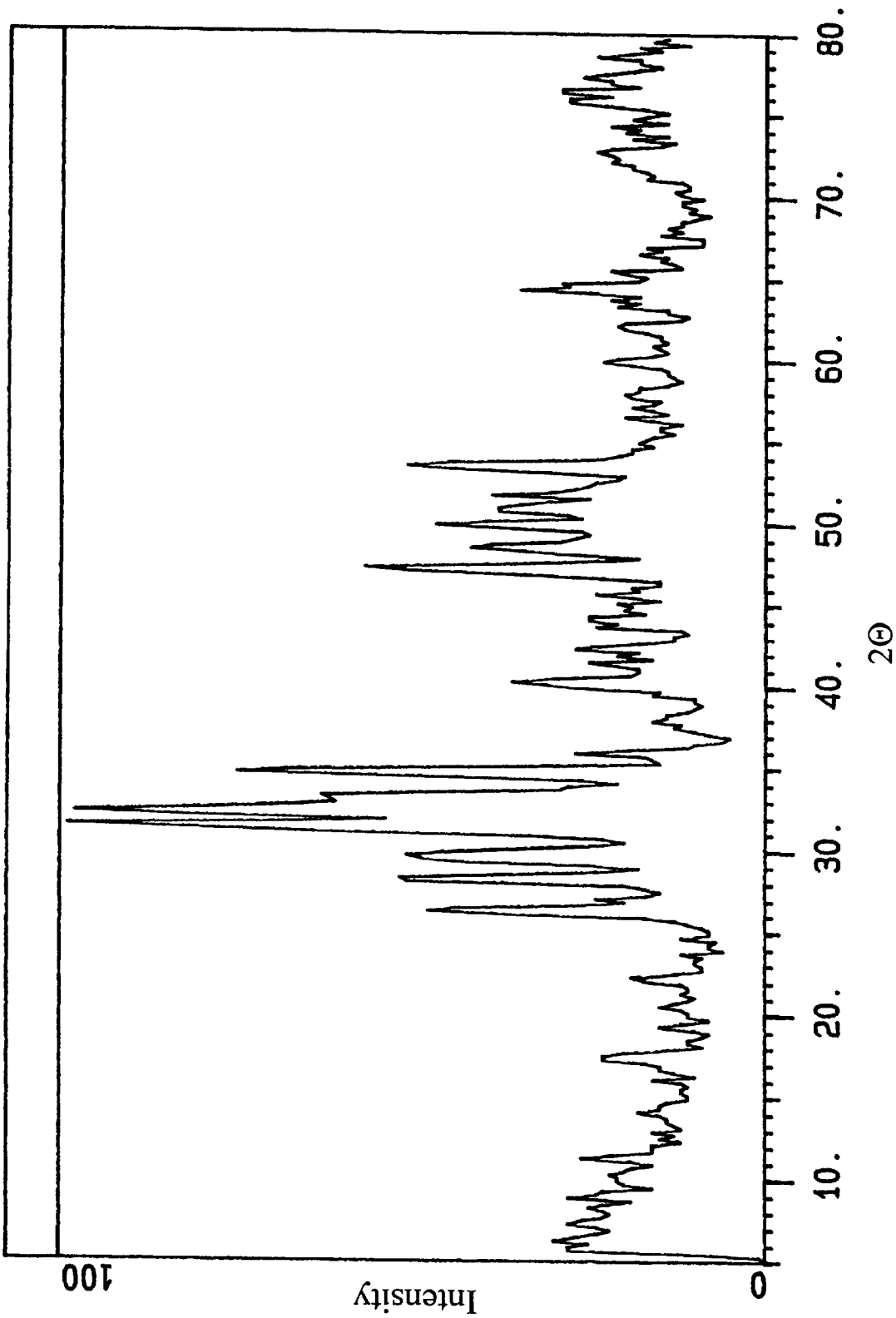
FIG. 5 is an X-ray Diffraction (XRD) plot of RPR generated calcium phosphate precursor mineral heated to 500° C. for 1 hour. The peak position and relative intensities indicate the presence of the crystal phases β-tricalcium phosphate (β-TCP)[major phase]+calcium pyrophosphate ($CaH_2P_2O_7$) [minor phase].
Figure 6:
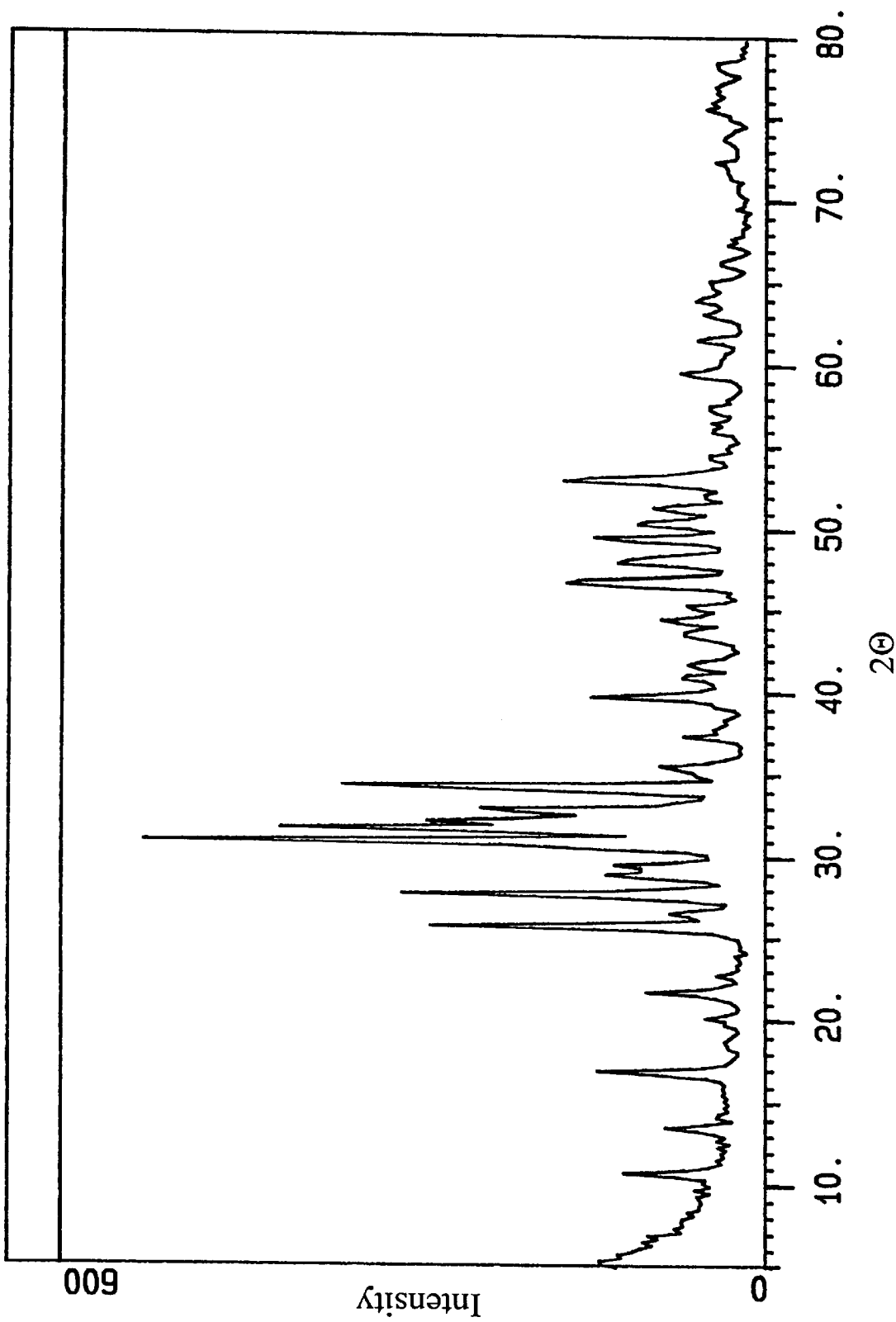
FIG. 6 is an X-ray Diffraction (XRD) plot of RPR generated calcium phosphate precursor mineral heated to 500° C. for 1 hour. The peak position and relative intensities indicate the presence of the crystal phases β-tricalcium phosphate (β-TCP) [major phase]+apatite ($Ca_5(PO_4)_3(OH)$) [minor phase].

Intermediate precursor mineral powders are homogeneously precipitated from solution. Moderate heat treatments, temperatures<500° C., can be used to further the transformation to various phosphate containing phases. Proper manipulations of chemistry and process have led to mono- and multi phasic compounds with unique crystal morphologies [FIGS. 1 & 2].

The nitrate/hypophosphite redox system involves a hypophosphite oxidation to phosphate ($P^{+1}$ to $P^{+5}$, a 4e$^-$ oxidation) as depicted in the following equations ( $E_o$/V from N. N. Greenwood and A. Earnshaw, "Oxoacids of phosphorus and their salts," in Chemistry of the Elements, pp 586–595 (1984), Pergamon Press):

| | Reduction potential at pH 0, 25° C. | |
|---|---|---|
| Reaction | $E_o/V$ | |
| $H_3PO_3 + 2H^+ + 2e^- = H_3PO_2 + H_2O$ | −0.499 | (1) |
| $H_3PO_4 + 2H^+ + 2e^- = H_3PO_3 + H_2O$ | −0.276 | (2) |
| $H_3PO_4 + 4H^+ + 4e^- = H_3PO_2 + 2H_2O$ | −0.775  Overall | (3) | and a nitrate reduction to $NO_x$ ($N^{+5}$ to $N^{+3}$ or $N^{+2}$, either a $2e^-$ or a $3e^-$ reduction) as depicted in the following equations;

| | Reduction potential at pH 0, 25° C. | |
|---|---|---|
| Reaction | $E_o/V$ | |
| $2NO_3^- + 4H^+ + 2e^- = N_2O_4 + 2H_2O$ | 0.803 | (4) |
| $NO_3^- + 3H^+ + 2e^- = HNO_2 + H_2O$ | 0.94 | (5) |
| $NO_3^- + 4H^+ + 3e^- = NO + 2H_2O$ | 0.957 | (6) |

Chemical reactions are conveniently expressed as the sum of two (or more) electrochemical half-reactions in which electrons are transferred from one chemical species to another. According to electrochemical convention, the overall reaction is represented as an equilibrium in which the forward reaction is stated as a reduction (addition of electrons), i.e.:

Oxidized species+$ne^-$=Reduced species

For the indicated equations at pH=0 and 25° C., the reaction is spontaneous from left to right if $E_o$ (the reduction potential) is greater than 0, and spontaneous in the reverse direction if $E_o$ is less than 0.

From the above reactions and associated electrochemical potentials, it is apparent that nitrate is a strong oxidant capable of oxidizing hypophosphite ($P^{+1}$) to phosphite ($P^{+3}$) or to phosphate ($P^{+5}$) regardless of the reduction reaction pathway, i.e., whether the reduction process occurs according to Equation 4, 5, or 6. If an overall reaction pathway is assumed to involve a combination of oxidation reaction (Eq.3) ($4e^-$ exchange) and reduction reaction (Eq.6) ($3e^-$ exchange), one can calculate that in order for the redox reaction to proceed to completion, 4/3 mole of $NO_3-$ must be reduced to NO per mole of hypophosphite ion to provide sufficient electrons. It is obvious to one skilled in the art that other redox processes can occur involving combinations of the stated oxidation and reduction reactions.

Different pairings of oxidation and reduction reactions can be used to generate products according to the spirit of this invention. Indeed, the invention generally allows for the in situ homogeneous production of simple or complex oxoacid anions in aqueous solution in which one or more nonmetallic elements such as Group 5B and 6B (chalcogenides), and 7B (halides) comprising the first oxoacid anion undergoes oxidation to generate the precipitant anionic species along with concurrent reduction of the nonmetallic element of a second, dissimilar oxoacid anion.

In each of the above scenarios, the key is the reduction-oxidation reaction at high ionic concentrations leading to the homogenous precipitation from solution of novel calcium phosphate powders. Never before in the literature has the ability to form such phases, especially calcium-phosphate phases, been reported under the conditions described in this invention.

The products can be adjusted by changing reaction conditions. Simple modification of the anion mixture (i.e. inclusion of acetate ion) in the starting solution can lead to a calcium phosphate phase with incorporated carbonate, which is most advantageous for in vivo conversion to bone, as bone itself is the carbonated version of hydroxyapatite mineral, with the substitution of the carbonate occurring in the phosphate lattice position, thus termed type-B HAp. Other beneficial substitutions are derived from F, fluorine, substitutions, leading to fluorapatite, as desired in dentrifices and tooth enamel. The sulfate anion may give rise to yet another beneficial calcium phase, whereby the hemihydrate species, $CaSO_4$-½$H_2O$, would provide an additional setting reaction when in contact with water, as with Plaster of Paris. Additional changes occur with the presence of other cations as dopants or major components.

Specific embodiments of the invention utilize the aforementioned processes to yield unique calcium phosphate precursor minerals that can be used to form a self-setting cement or paste. Once placed in the body, these calcium phosphate cements (CPC) will be resorbed and remodeled (converted) to bone. A single powder consisting of biphasic minerals of varying Ca/P ratio can be mixed to yield self-setting pastes that convert to type-B carbonated apatite (bone mineral precursor) in vivo.

The remodeling behavior of a calcium phosphate bioceramic to bone is dictated by the energetics of the surface of the ceramic and the resultant interactions with osteoclastic cells on approach to the interface. Unique microstructures can yield accelerated reactivity and, ultimately, faster remodeling in vivo. The compositional flexibility in the fine particles of this invention offers adjustable reactivity in vivo. The crystallite size and surface properties of the resultant embodiments of this invention are more similar to the scale expected and familiar to the cells found in the body. Mixtures of powders derived from the processes of this invention have tremendous utility as calcium phosphate cements (CPCs).

For example, calcium phosphate particles prepared in accordance with this invention can be used in any of the orthopaedic or dental procedures known for the use of calcium phosphate; the procedures of bone filling defect repair, oncological defect filling, craniomaxillofacial void filling and reconstruction, dental extraction site filling, and potential drug delivery applications.

Numerous uses are anticipated. The oxidizing agents, reducing agents, ratios, co-reactants and other adducts, products and exemplary uses will be understood by inorganic chemists from a review of the aforementioned chemical reactions. Calcium phosphates are indicated for biological restorations, dental restorations, bioseparations media, and ion or protein chromatography. Transition metal phosphates (Sc, Ti, V, Cr, Mn, Fe, Co, Ni, Cu, and Zn) have numerous potential uses as pigments, phosphors, catalysts, electromagnetic couplers, microwave couplers, inductive elements, zeolites, glasses, nuclear waste containment systems and coatings. Addition of rare-earths phosphates can lead to uses as intercalation compounds, catalysts, glasses and ceramics, radiopharmaceuticals, pigments and phosphors, medical imaging agents, nuclear waste solidification, electro-optics, electronic ceramics, and surface modifications.

Aluminum and zirconium phosphates are ideal candidates for surface protective coatings, abrasive particles, polishing agents, cements, and filtration products in either granular form or as coatings. The alkali (Na, K, Rb, Cs) and alkaline-earth (Be, Mg, Ca, Sr, Ba) phosphates would generate ideal low temperature glasses, ceramics, biomaterials, cements, glass to metal seals, and other numerous glass-ceramic materials, such as porcelains, dental glasses, electro-optic glasses, laser glasses, specific refractive index glasses and optical filters.

EXAMPLES

Example 1

Novel Low Temperature Calcium Phosphate Powder Preparation

An aqueous solution of 8.51 g 50 wt % hypophosphorus acid, $H_3PO_2$ (Alfa/Aesar reagent #14142, CAS #6303-21-5), equivalent to 71.95 wt % $[PO_4]^{-3}$ was combined with 8.00 g distilled water to form a clear, colorless solution contained in a 250 ml Pyrex beaker. To this solution was added 22.85 g calcium nitrate tetrahydrate salt, $Ca(NO_3)_2.4H_2O$ (ACS reagent, Aldrich Chemical Co., Inc. #23,712-4, CAS #13477-34-4) equivalent to 16.97 wt % Ca. The molar ratio of Ca/phosphate in this mixture was 3/2 and the equivalent solids level [as $Ca_3(PO_4)_2$] was 25.4 wt %. Endothermic dissolution of the calcium nitrate tetrahydrate proceeded under ambient temperature conditions, eventually forming a homogeneous solution. Warming of this solution above 25° C. initiated a reaction in which the solution vigorously bubbled while evolving red-brown acrid fumes characteristic of $NO_{x(g)}$. The sample turned into a white, pasty mass which foamed and pulsed with periodic expulsion of $NO_{x(g)}$. After approximately two minutes, the reaction was essentially complete, leaving a white, pasty mass which was warm to the touch. After cooling to room temperature, the solid (A) was stored in a polyethylene vial.

Three days after its preparation, a few grams of the damp, pasty solid were immersed in 30 ml distilled water in order to "wash out" any unreacted, water soluble components. The solid was masticated with a spatula in order to maximize solid exposure to the water. After approximately 15 minutes, the solid was recovered on filter paper and the damp solid (B) stored in a polyethylene vial.

X-ray diffraction (XRD) patterns were obtained from packed powder samples using the Cu-Kα line (λ=1.7889 Angstrom) from a Rigaku Geigerflex instrument run at 45 kV/30 mA using a 3 degree/minute scan rate over the 2θ angular range from 15–50° or broader. Samples were run either as prepared or following heat treatment in air in either a Thermolyne type 47900 or a Ney model 3-550 laboratory furnace. XRD results are as follows (see FIGS. 3, 4, 5, and 6):

| Sample | Heat treatment | Major phase | Minor phase |
|---|---|---|---|
| Unwashed (A) | As prepared | Undetermined | — |
| Unwashed (A) | 300° C., 1 h | Monetite [$CaHPO_4$] | — |
| Unwashed (A) | 500° C., 1 h | Whitlockite [β-$Ca_3(PO_4)_2$] | $CaH_2P_2O_7$ |
| Unwashed (A) | 700° C., 1 h | Whitlockite [β-$Ca_3(PO_4)_2$] + HAp[$Ca_5(PO_4)_3(OH)$] | |
| Washed (B) D.I. water | As prepared | Monetite [$CaHPO_4$] | |
| Washed (B) D.I. water | 100° C., 1 h | Monetite [$CaHPO_4$] | |

Considerable amounts of $NO_{x(g)}$ were evolved during firing of the samples at or above 300° C.

Example 2

Novel Low Temperature Calcium Phosphate Powder Preparation

Example 1 was repeated using five times the indicated weights of reagents. The reactants were contained in a 5½" diameter Pyrex crystallizing dish on a hotplate with no agitation. Warming of the homogeneous reactant solution above 25° C. initiated an exothermic reaction which evolved red-brown acrid fumes characteristic of $NO_{x(g)}$. Within a few seconds following onset of the reaction, the sample turned into a white, pasty mass which continued to expel $NO_{x(g)}$ for several minutes. After approximately five minutes, the reaction was essentially complete leaving a damp solid mass which was hot to the touch. This solid was cooled to room temperature under ambient conditions for approximately 20 minutes and divided into two portions prior to heat treatment.

Heat treatment and X-ray diffraction of this solid were conducted as described in Example 1. Following heat treatment in air, XRD indicated the fired solids to be composed of:

| Sample | Heat treatment | Major phase | Minor phase |
|---|---|---|---|
| A | 500° C., 1 h | Whitlockite [β-$Ca_3(PO_4)_2$] | HAp [$Ca_5(PO_4)_3(OH)$] |
| B | 700° C., 1 h | HAp [$Ca_5(PO_4)_3(OH)$] | Whitlockite [β-$Ca_3(PO_4)_2$] |

Example 3

Novel Low Temperature Calcium Phosphate Powder Preparation

An aqueous solution of 8.51 g 50 wt % $H_3PO_2$ was combined with 8.00 g of 25.0 wt % aqueous solution of calcium acetate monohydrate, $Ca(O_2CCH_3)_2.H_2O$ (ACS reagent, Aldrich Chemical Co., Inc. #40,285-0, CAS 5743-26-0), equivalent to 5.69 wt % Ca, to give a clear, colorless solution contained in a 250 ml Pyrex beaker. To this solution was added 20.17 g $Ca(NO_3)_2.4H_2O$ salt. The molar ratio of Ca/phosphate in this mixture was 3/2 and the equivalent solids level [as $Ca_3(PO_4)_2$] was 27.3 wt %. Endothermic dissolution of the calcium nitrate tetrahydrate salt proceeded giving a homogeneous solution once the sample warmed to room temperature. Further warming of this solution to >25° C. on a hotplate initiated a reaction which proceeded as described in Example 1. After approximately three minutes, the reaction was essentially complete leaving a moist, white, crumbly solid which was hot to the touch and which smelled of acetic acid. After cooling to room temperature, the solid was stored in a polyethylene vial.

Heat treatment and X-ray diffraction analysis of this solid were conducted as described in Example 1. Following heat treatment in air at 500° C. for either 0.5 or 1 hour, XRD indicated the solid to be composed of whitlockite as the primary phase along with hydroxylapatite as the secondary phase. XRD results indicate that the relative ratio of the two calcium phosphate phases was dependent on the duration of the heat treatment and the presence of the acetate anion, but no attempts were made to quantify the dependence.

| Heated to 500° C., 1 h | (Major) | Whitlockite [β-$Ca_3(PO_4)_2$] |
|---|---|---|
| | (minor) | $Ca_5(PO_4)_{3-x}(CO_3)_x(OH)$ |

Figure 7:
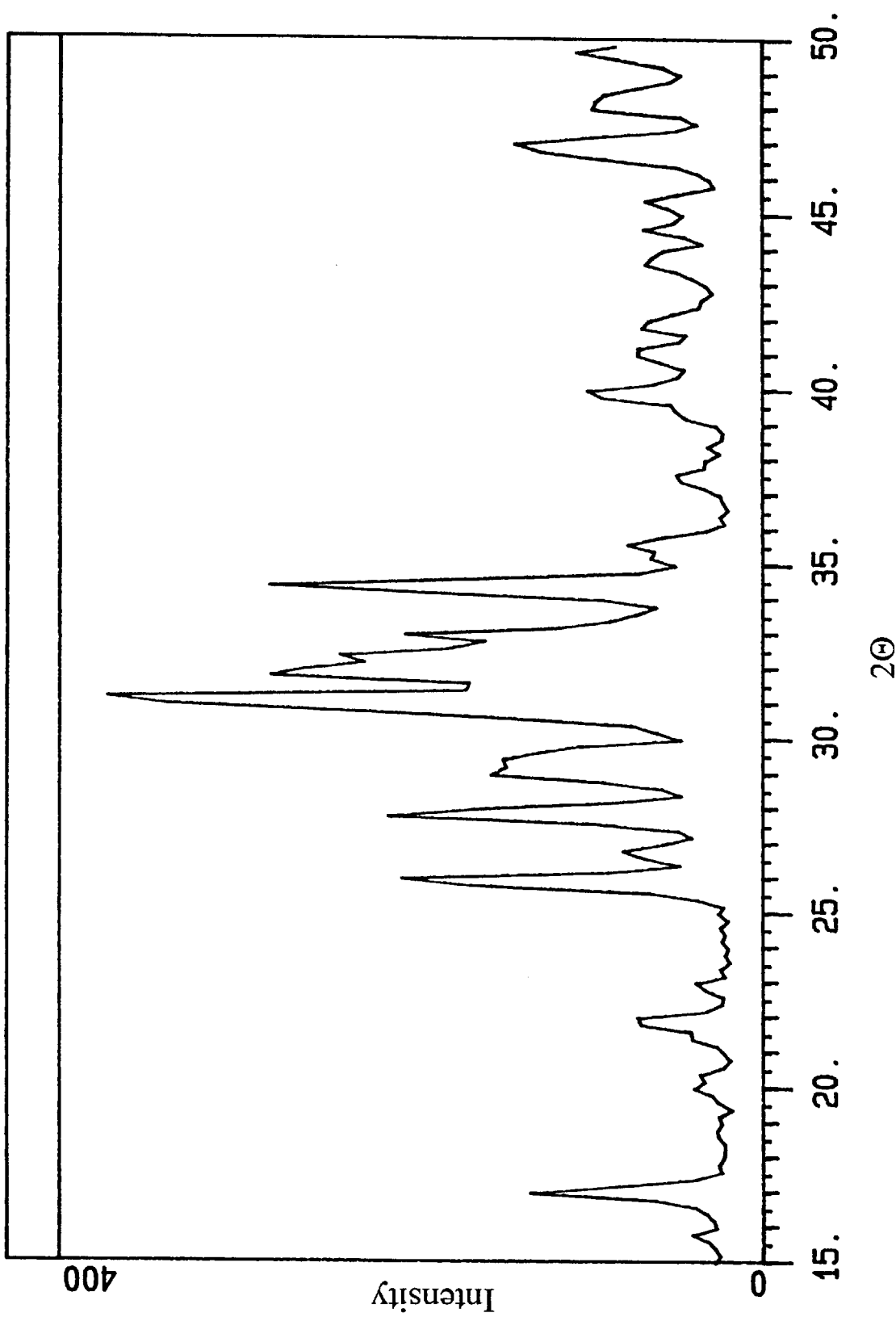
FIG. 7 is an X-ray Diffraction (XRD) plot of RPR generated calcium phosphate precursor mineral, without added [$CO_3$]$^{2-}$, heated to 500° C. for 1 hour. The peak position and relative intensities indicate the presence of the crystal phases β-tricalcium phosphate (β-TCP)[major phase]+apatite ($Ca_5(PO_4)_3(OH)$) [minor phase].
Figure 8:
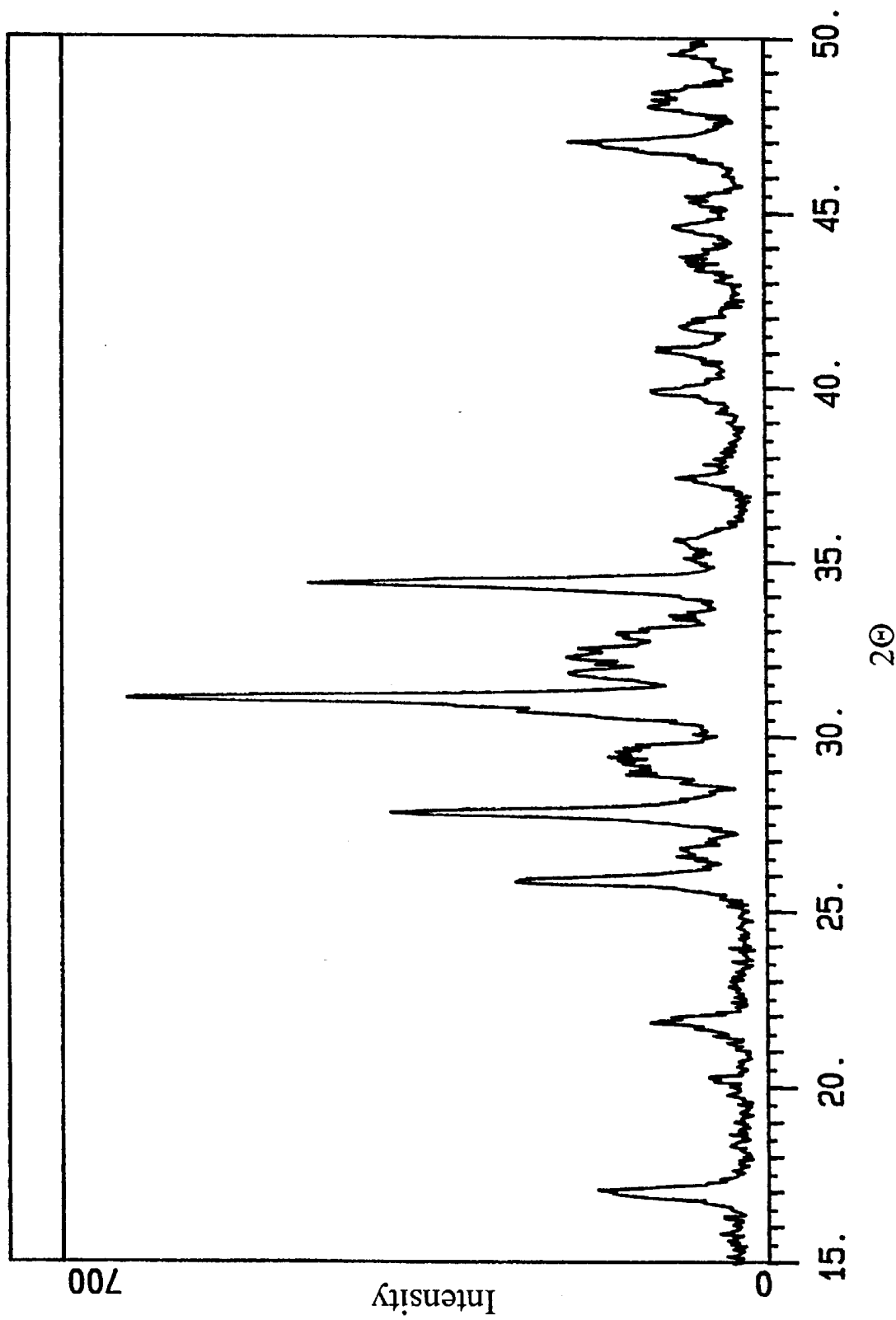
FIG. 8 is an X-ray Diffraction (XRD) plot of RPR generated calcium phosphate precursor mineral, with added [$CO_3$]$^{2-}$, heated to 500° C. for 1 hour. The peak position and relative intensities indicate the presence of the crystal phases β-tricalcium phosphate (β-TCP)[major phase]+apatite ($Ca_5$ $(PO_4)_3(OH)$) [minor phase]. The spectrum shows a significant difference in the intensity of the HAp peaks, as compared to that in FIG. 7.

Comparing the XRD spectra in FIG. 7 and 8 shows the difference in the amount of HAp-$Ca_5(PO_4)_{3-x}(CO_3)_x(OH)$ phase present for each minor phase from Example 1 (which had no acetate) and Example 3 (acetate present), respectively. This is indicative of the counteranion effect on crystal formation.

Figure 9:
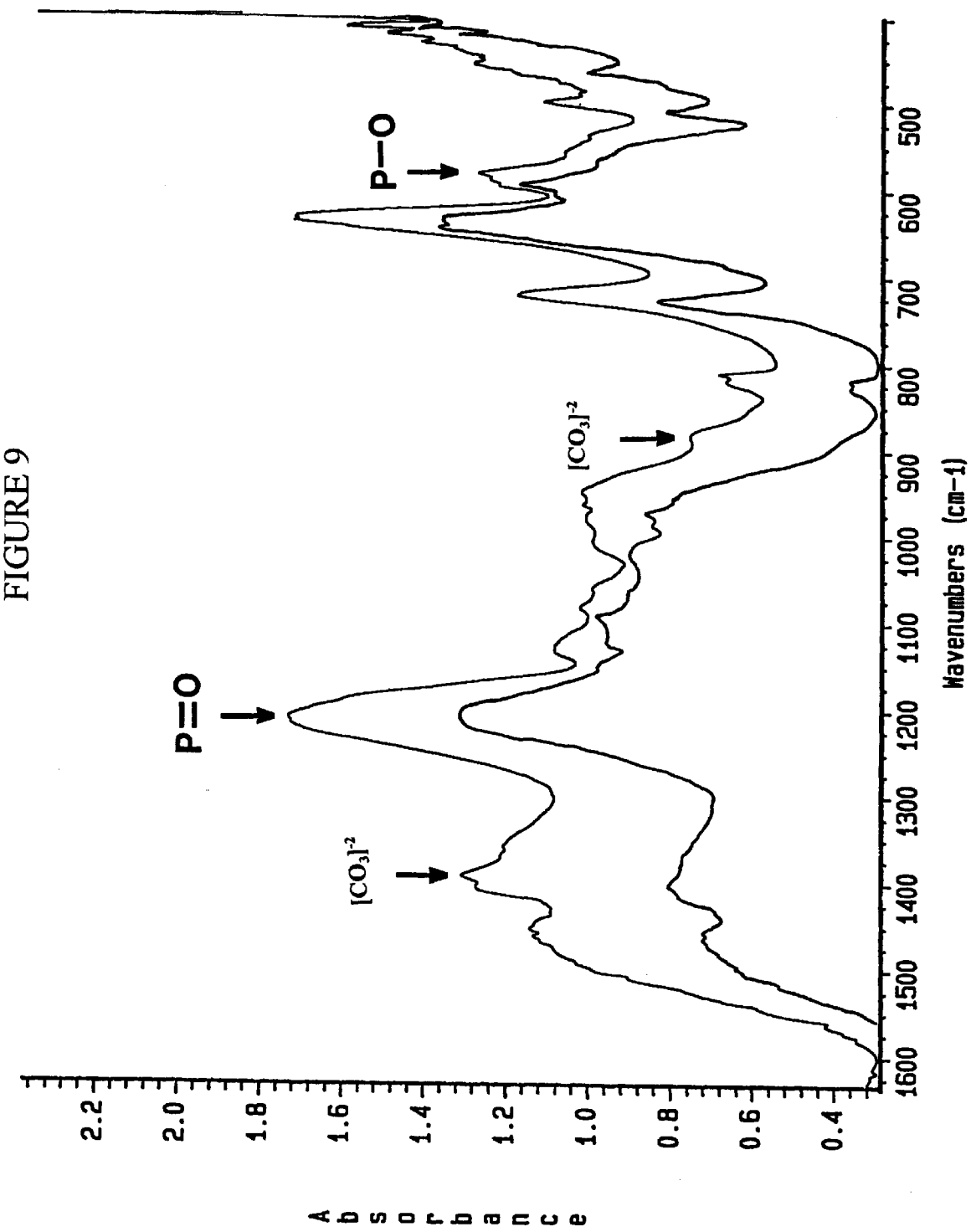
FIG. 9 depicts Fourier Transform Infrared (FTIR) spectra of calcium phosphate as used for FIG. 8, indicating the presence of [$CO_3$]$^{2-}$ vibrations, at 880, 1400, and 1450 cm$^{-1}$, and associated P—O, P=O vibrations, at 540–610, 1100–1250 cm$^{-1}$ respectively. A second FTIR plot (lower plot) of the material of FIG. 7 is also depicted to show lack of carbonate peaks at 880 cm$^{-1}$.

Fourier Transform Infrared (FTIR) spectra were obtained using a Nicolet instrument (model number 5DXC) run in the diffuse reflectance mode over the range of 400 to 4000 cm$^{-1}$. The presence of the carbonated form of HAp is confirmed by the FTIR spectra in FIG. 9 (400 to 1600 cm$^{-1}$), which indicates the presence of peaks characteristic of [PO$_4$]$^-$ (580–600, 950–1250 cm$^{-1}$) and of [CO$_3$]$^{-2}$ (880, 1400, & 1450 cm$^{-1}$). The P=O stretch, indicated by the strong peak at 1150–1250 cm$^{-1}$, suggests a structural perturbation of hydroxyapatite by the carbonate ion.

Example 4

Colloidal SiO$_2$ added to calcium phosphate mixtures via RPR

An aliquot of 8.00 g 34.0 wt % SiO$_2$ hydrosol (Nalco Chemical Co., Inc. #1034A, batch #B5G453C) was slowly added to 8.51 g 50 wt % aqueous solution of H$_3$PO$_2$ with rapid stirring to give a homogeneous, weakly turbid colloidal dispersion. To this dispersion was added 22.85 g Ca(NO$_3$)$_2$.4H$_2$O salt such that the molar ratio of calcium/phosphate in the mixture was 3/2. Endothermic dissolution of the calcium nitrate tetrahydrate proceeded giving a homogeneous colloidal dispersion once the sample warmed to room temperature. The colloidal SiO$_2$ was not flocculated despite the high acidity and ionic strength in the sample. Warming of the sample on a hotplate to >25° C. initiated a reaction as described in Example 1. The resultant white, pasty solid was stored in a polyethylene vial.

Heat treatment and X-ray diffraction of this solid were conducted as described in Example 1. Following heat treatment in air at 500° C. for 1.0 hour, XRD indicated the solid to be composed of whitlockite plus hydroxyapatite.

| | | |
|---|---|---|
| Heated to 300° C., 2 h | (Major) | Calium pyrophosphate [Ca$_2$P$_2$O$_7$] |
| | (minor) | Octacalcium phosphate [Ca$_4$H(PO$_4$)$_3$.2H$_2$O] |
| Heated to 500° C., 1 h | (Major) | Whitlockite [β-Ca$_3$(PO$_4$)$_2$] |
| | (minor) | HAp [Ca$_5$(PO$_4$)$_3$(OH)] |

Example 5

Novel Low Temperature Calcium Phosphate Powder Preparation

Example 1 was repeated with the addition of 10.00 g dicalcium phosphate dihydrate, DCPD, CaHPO4.2H$_2$O (Aldrich Chemical Co., Inc. #30,765-3, CAS #7789-77-7) to the homogeneous solution following endothermic dissolution of the calcium nitrate salt. The DCPD was present both as suspended solids and as precipitated material (no agitation used). Warming of the sample to >25° C. initiated an exothermic reaction as described in Example 1, resulting in the formation of a white, pasty solid. Heat treatment and X-ray diffraction of this solid were conducted as described in Example 1. Following heat treatment in air at 500° C. for 1 hour, XRD indicated the solid to be composed of whitlockite as the primary phase along with calcium pyrophosphate (Ca$_2$P$_2$O$_7$) as the secondary phase.

| | | |
|---|---|---|
| Heated to 500° C., 1 h | (Major) | Whitlockite [β-Ca$_3$(PO$_4$)$_2$] |
| | (minor) | Ca$_2$P$_2$O$_7$ |

Example 6

Novel Low Temperature Zinc Phosphate Powder Preparation

An aqueous solution of 8.51 g 50 wt % H$_3$PO$_2$ in 8.00 g distilled water was prepared as described in Example 1. To this solution was added 28.78 g zinc nitrate hexahydrate salt, Zn(NO$_3$)$_2$.6H$_2$O (ACS reagent, Aldrich Chemical Co., Inc. #22,873-7, CAS #10196-18-6), equivalent to 21.97 wt % Zn. The molar ratio of Zn/phosphate in this mixture was 3/2 and the equivalent solids level [as Zn$_3$(PO$_4$)$_2$] was 27.5 wt %. Endothermic dissolution of the zinc nitrate hexahydrate proceeded giving a homogeneous solution once the sample warmed to room temperature. Further warming of this solution to >25° C. on a hotplate initiated a reaction in which the solution vigorously evolved red-brown acrid fumes of NO$_{x(g)}$. The reaction continued for approximately 10 minutes while the sample remained a clear, colorless solution, abated somewhat for a period of five minutes, then vigorously resumed finally resulting in the formation of a mass of moist white solid, some of which was very adherent to the walls of the Pyrex beaker used as a reaction vessel. The hot solid was allowed to cool to room temperature and was stored in a polyethylene vial.

Figure 10:
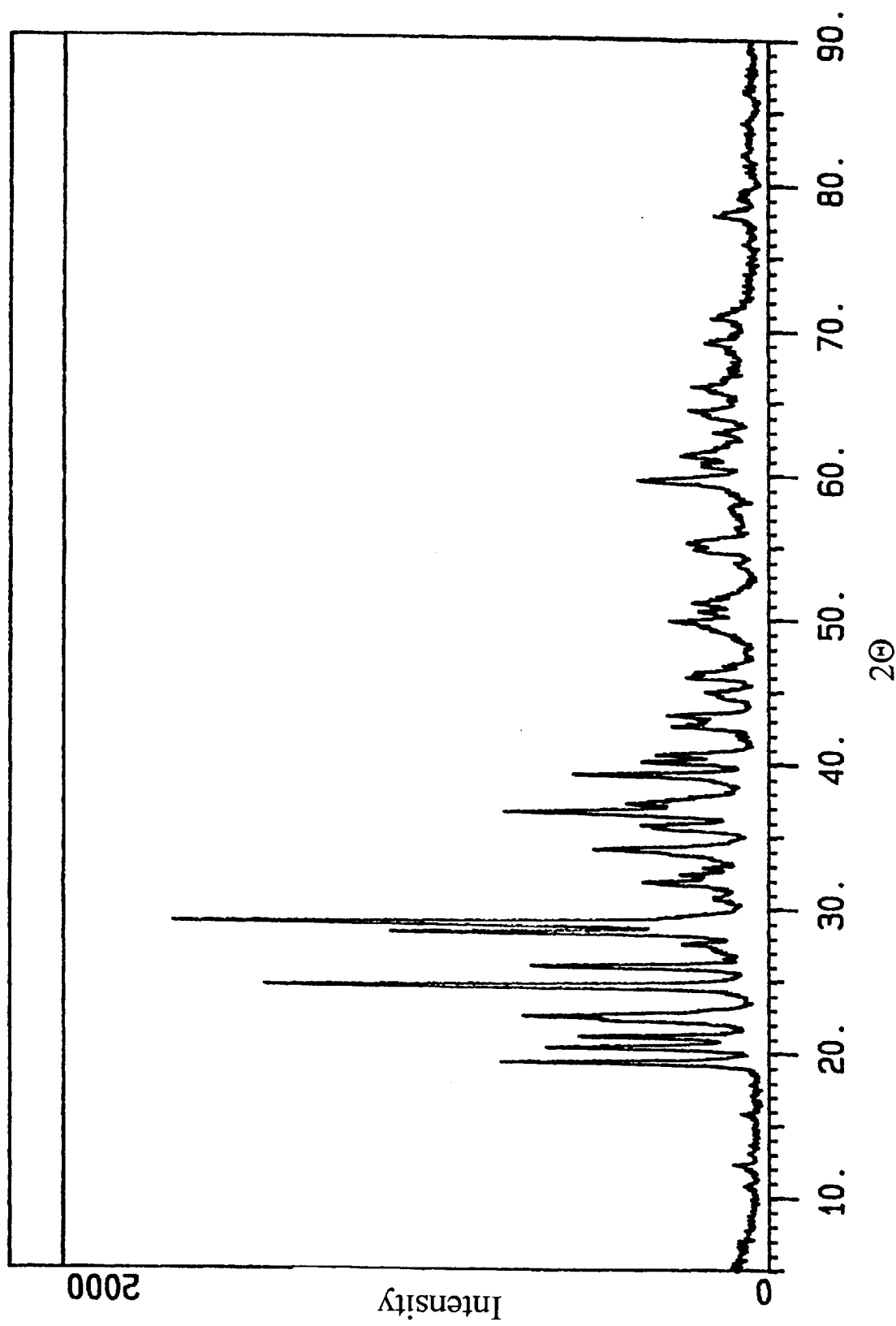
FIG. 10 is an X-ray Diffraction (XRD) plot of RPR generated zinc phosphate precursor mineral heated to 500° C. for 1 hour. The peak position and relative intensities indicate the presence of the crystal phase $Zn_3(PO_4)_2$.

Heat treatment and X-ray diffraction of this solid were conducted as described in Example 1. Following heat treatment in air at 500° C. for 1 hour, XRD indicated the solid to be composed of Zn$_3$(PO$_4$)$_2$ (see FIG. 10).

| | | |
|---|---|---|
| Heated to 500° C., 1 h | (Major) | Zn$_3$(PO$_4$)$_2$ |

Example 7

Novel Low Temperature Iron Phosphate Powder Preparation

An aqueous solution of 17.50 g 50 wt % H$_3$PO$_2$ was combined with 15.00 g distilled water to form a clear, colorless solution contained in a 250 ml Pyrex beaker on a hotplate/stirrer. To this solution was added 53.59 g ferric nitrate nonahydrate salt, Fe(NO$_3$)$_3$-9H$_2$O (ACS reagent, Alfa/Aesar reagent #33315, CAS #7782-61-8), equivalent to 13.82 wt % Fe. The molar ratio of Fe/phosphate in this mixture was 1/1 and the equivalent solids level [as FePO$_4$] was 23.2 wt %. Endothermic dissolution of the ferric nitrate nonahydrate salt proceeded partially with gradual warming of the reaction mixture, eventually forming a pale lavender solution plus undissolved salt. At some temperature >25° C., an exothermic reaction was initiated which evolved NO$_{x(g)}$. This reaction continued for approximately 15 minutes during which time the reaction mixture became syrup-like in viscosity. With continued reaction, some pale yellow solid began to form at the bottom of the beaker. After approximately 40 minutes of reaction, the sample was allowed to cool to room temperature. The product consisted of an inhomogeneous mixture of low density yellow solid at the top of the beaker, a brown liquid with the consistency of caramel at the center of the product mass, and a sand colored solid at the bottom of the beaker. The solids were collected as separate samples insofar as was possible.

Figure 11:
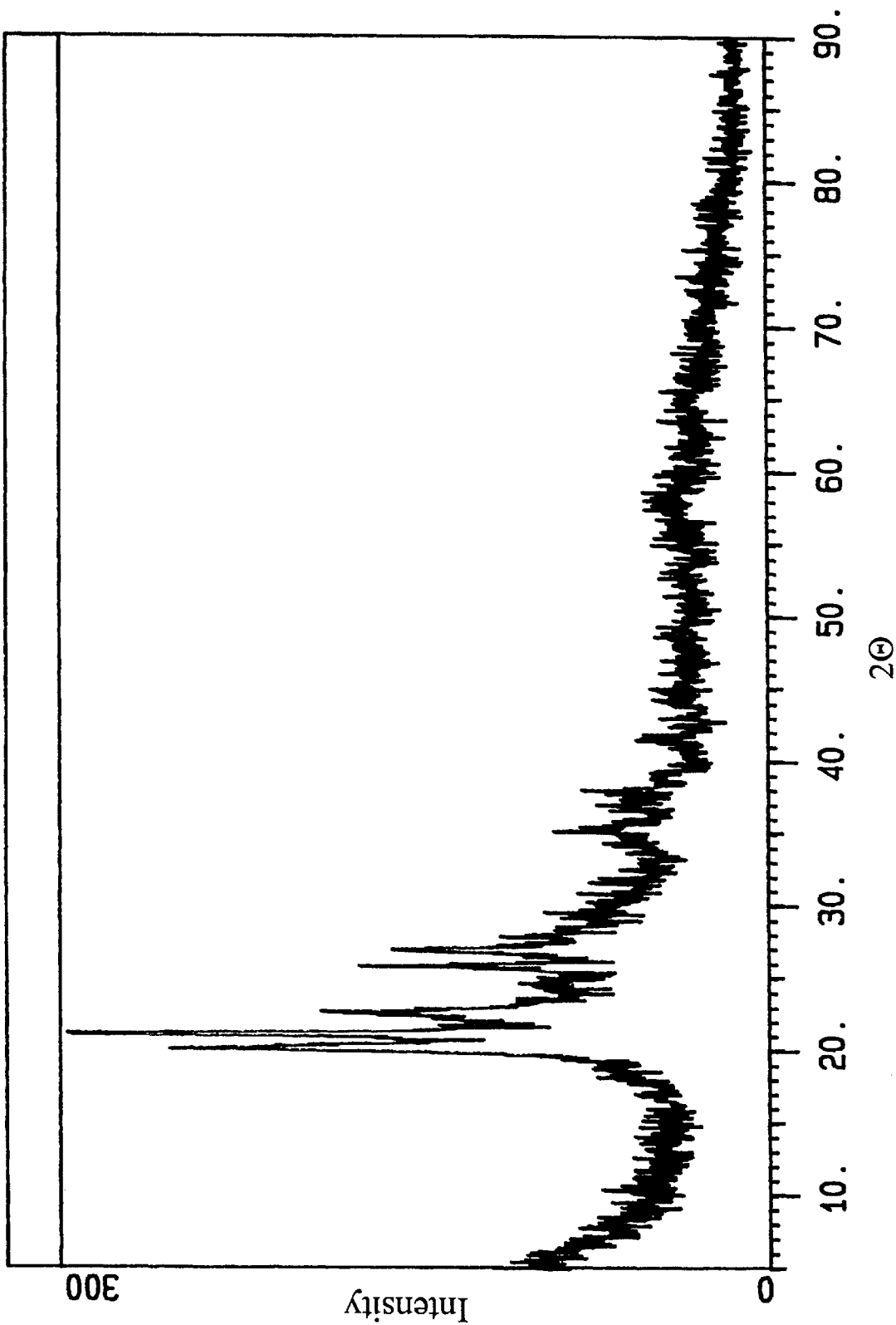
FIG. 11 is an X-ray Diffraction (XRD) plot of RPR generated iron phosphate precursor mineral heated to 500° C. for 1 hour. The peak position and relative intensities indicate the presence of the crystal phase Graftonite [$Fe_3$ $(PO_4)_2$].

Heat treatment and X-ray diffraction of the solid collected from the top of the beaker were conducted as described in Example 1. Following heat treatment in air at 500° C. for 1 hour, XRD indicated the solid to be composed of graftonite [$Fe_3(PO_4)_2$] plus some amorphous material, suggesting that the heat treatment was not sufficient to induce complete sample crystallization (see FIG. 11).

| | | |
|---|---|---|
| Heated to 500° C., 1 h | (Major) | Graftonite [$Fe_3(PO_4)_2$] |

Some mechanism apparently occurs by which $Fe^{3+}$ was reduced to $Fe^{2+}$.

Example 8

Novel Low Temperature Calcium Phosphate Powder Preparation

An aqueous solution of 19.41 g 50 wt % $H_3PO_2$ was combined with 5.00 g distilled water to form a clear, colorless solution contained in a 250 ml Pyrex beaker. To this solution was added 34.72 g $Ca(NO_3)_2 \cdot 4H_2O$. The molar ratio of Ca/phosphate in this mixture was 1/1 and the equivalent solids level [as $CaHPO_4$] was 33.8 wt %. Endothermic dissolution of the calcium nitrate tetrahydrate proceeded under ambient temperature conditions, eventually forming a homogeneous solution once the sample warmed to room temperature. Warming of this solution above 25° C. initiated a vigorous exothermic reaction which resulted in the evolution of $NO_{x(g)}$, rapid temperature increase of the sample to >100° C., and extensive foaming of the reaction mixture over the beaker rim, presumably due to flash boiling of water at the high reaction temperature. After cooling to room temperature, the reaction product was collected as a dry, white foam which was consolidated by crushing to a powder.

Heat treatment and X-ray diffraction of this solid were conducted as described in Example 1. Results are as follows:

| | | |
|---|---|---|
| Heated to 300° C., 2 h | (Major) | $Ca_2P_2O_7$ |
| | (minor) | Octacalcium phosphate [$Ca_4H(PO_4)_3 \cdot 2H_2O$] |
| Heated to 500° C., 1 h | (Major) | $Ca_2P_2O_7$ |

Example 9

Novel Low Temperature Calcium Phosphate Powder Preparation

Example 3 was repeated using ten times the indicated weights of reagents. The reactants were contained in a 5½" diameter Pyrex crystallizing dish on a hotplate/stirrer. The reactants were stirred continuously during the dissolution and reaction stages. The chemical reaction initiated by heating the solution to >25° C. resulted in the evolution of $NO_{x(g)}$ for several minutes with no apparent effect on the stability of the system, i.e. the solution remained clear and colorless with no evidence of solid formation. After abating for several minutes, the reaction resumed with increased intensity resulting in the voluminous generation of $NO_{x(g)}$ and the rapid appearance of a pasty white solid material. The reaction vessel and product were both hot from the reaction exotherm. The product was cooled in air to a white crumbly solid which was stored in a polyethylene vial.

Heat treatment and X-ray diffraction of this solid were conducted as described in Example 1. Following heat treatment in air at 500° C. for either 0.5 or 1 hour, XRD indicated the solid to be composed of whitlockite as the primary phase along with hydroxyapatite as the secondary phase. XRD results indicate that the relative ratio of the two calcium phosphate phases was dependent on the duration of the heat treatment, but no attempts were made to quantify the dependence.

| | | |
|---|---|---|
| Heated to 500° C., 1 h | (Major) | Whitlockite [$\beta$-$Ca_3(PO_4)_2$] |
| | (minor) | $Ca_5(PO_4)_{3-x}(CO_3)_x(OH)$ |

Example 10

Novel Low Temperature Aluminum Phosphate Powder Preparation

An aqueous solution of 10.82 g 50 wt % $H_3PO_2$ was combined with 2.00 g distilled water to form a clear, colorless solution contained in a 250 ml beaker. To this solution was added 30.78 g aluminum nitrate nonahydrate salt, $Al(NO_3)_3 \cdot 9H_2O$ (ACS reagent, Alfa/Aesar reagent #36291, CAS #7784-27-2), equivalent to 7.19 wt % Al. The molar ratio of Al/phosphate in this mixture was 1/1 and the equivalent solids level [as $AlPO_4$] was 22.9 wt %. Endothermic dissolution of the aluminum nitrate nonahydrate proceeded giving a homogeneous solution once the sample warmed to room temperature. Further warming of this solution to >25° C. on a hotplate initiated a reaction in which the solution vigorously evolved red-brown acrid fumes of $NO_{x(g)}$. Reaction continued for approximately 15 minutes during which the solution viscosity increased considerably prior to formation of a white solid.

Figure 12:
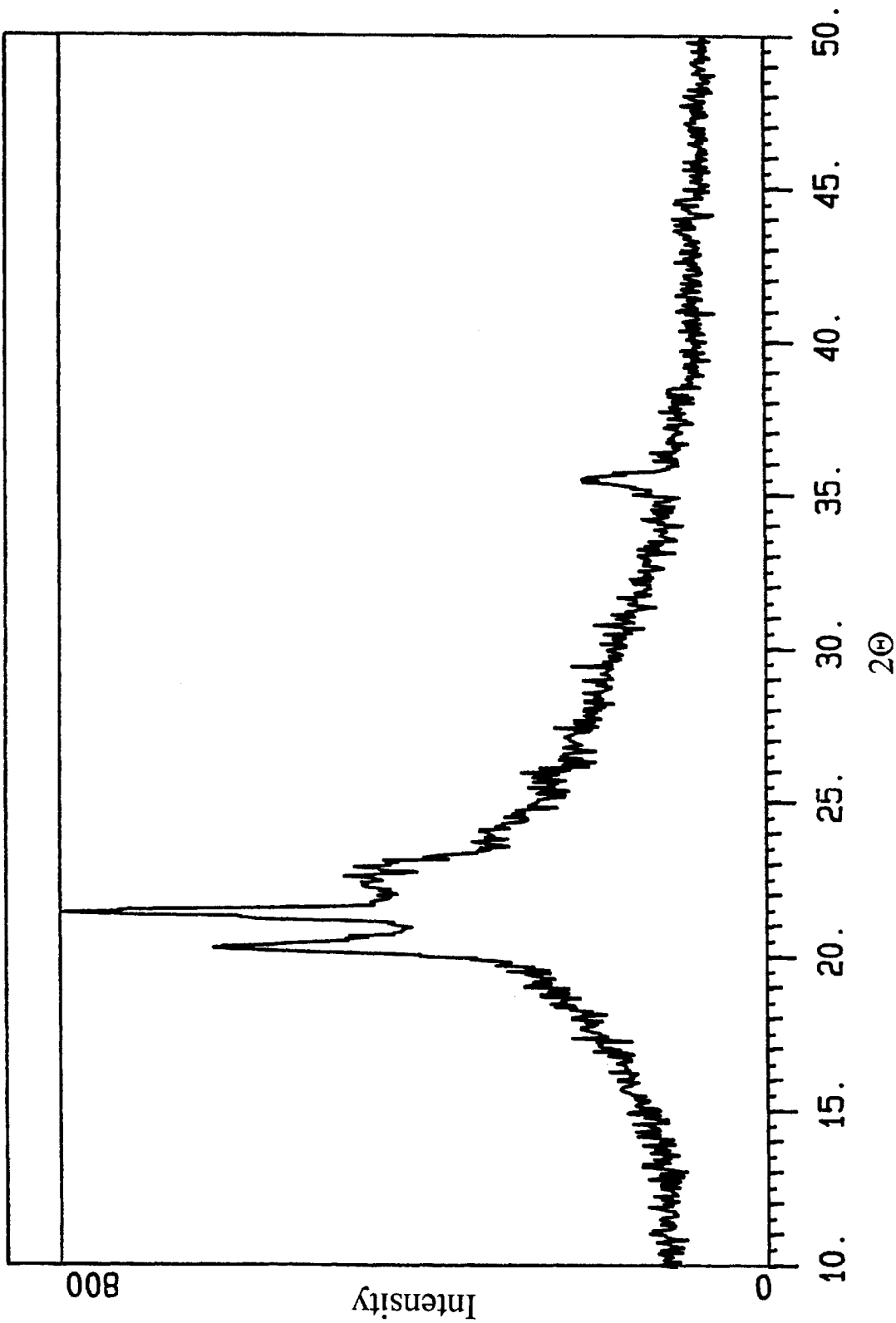
FIG. 12 is an X-ray Diffraction (XRD) plot of RPR generated aluminum phosphate precursor mineral heated to 500° C. for 1 hour. The peak position and relative intensities indicate the presence of the crystal phase $AlPO_4$.

Heat treatment and X-ray diffraction of this solid were conducted as described in Example 1. Following heat treatment in air at 500° C. for 0.5 hour, XRD indicated the solid to be composed of $AlPO_4$ plus some amorphous material, suggesting that the heat treatment was not sufficient to induce complete sample crystallization (see FIG. 12).

Example 11

Novel Low Temperature Calcium Phosphate Powder Preparation

An aqueous solution of 8.06 g 50 wt % $H_3PO_2$ reagent was combined with 6.00 g distilled water to form a clear, colorless solution in a 250 ml Pyrex beaker on a hotplate/stirrer. To this solution was added 19.23 g $Ca(NO_3)_2 \cdot 4H_2O$. The molar ratio of Ca/phosphate in this sample was 4/3 and the equivalent solids [as octacalcium phosphate, $Ca_8H_2(PO_4)_6 \cdot 5H_2O$] was 30.0 wt %. Endothermic dissolution of the calcium nitrate tetrahydrate proceeded under ambient conditions, eventually forming a homogeneous solution once the sample warmed to room temperature. Warming of the solution above 25° C. initiated a vigorous exothermic reaction as described in Example 1. After approximately three minutes, the reaction was essentially complete leaving a moist, white, pasty solid.

Heat treatment and X-ray diffraction of this solid were conducted as described in Example 1. Following heat treatment in air at 500° C. for 0.5 hour, XRD indicated the solid to be composed of whitlockite as the primary phase along with hydroxyapatite as the secondary phase. There was no evidence for the formation of octacalcium phosphate (OCP), despite the initial sample stoichiometry. This result suggests that (a) alternate heat treatments are necessary to crystallize OCP and/or (b) excess Ca is present in the intermediate powder.

| Heated to 500° C., 0.5 h | (Major) | Whitlockite [$\beta$-Ca$_3$(PO$_4$)$_2$] |
|---|---|---|
| | (minor) | HAp Ca$_5$(PO$_4$)$_3$(OH) |

Example 12

Novel Low Temperature Calcium Phosphate Powder Preparation

Example 11 was repeated except that no distilled water was used in preparation of the reaction mixture. Warming of the homogeneous solution above 25° C. initiated an exothermic reaction as described in Example 11. After approximately three minutes, the reaction was essentially complete leaving a moist, pasty, white solid.

Heat treatment and X-ray diffraction of this solid were conducted as described in Example 1. Following heat treatment in air at 500° C. for 0.5 hour, XRD indicated the solid to be composed of calcium pyrophosphate (Ca$_2$P$_2$O$_7$).

| Heated to 500° C., 0.5 h | (Major) | Ca$_2$P$_2$O$_7$ |
|---|---|---|

Example 13

Novel Low Temperature Hydrothermal (HYPR) Calcium Phosphate Powder Preparation An aqueous solution of 50 wt % calcium nitrate tetrahydrate, Ca(NO$_3$)$_2$-4H$_2$O (ACS reagent, Aldrich Chemical Co., Inc. #23,712-4, CAS #13477-34-4) was prepared by dissolving 250.0 g of the salt in 250.0 g distilled water. This solution was equivalent to 8.49 wt % Ca. A total of 47.0 g of this solution was added, with rapid agitation, to an aqueous solution of 50 wt % sodium hypophosphite monohydrate, NaH$_2$PO$_2$—H$_2$O (Alfa/Aesar reagent #14104, CAS #10039-56-2) also prepared by dissolving 250.0 g of the salt in 250.0 g distilled water. The sodium hypophosphite solution was equivalent to 44.80 wt % [PO$_4$]$^{-3}$. The clear, colorless solution of calcium nitrate and sodium hypophosphite was then diluted with 40.3 g distilled water. The molar ratio of Ca/phosphate in this mixture was 5/3, and the equivalent solids level [as Ca$_5$(PO$_4$)$_3$(OH) (hydroxyapatite)] was 10.0 wt %. The sample was hydrothermally treated using a 300 cc volume stirred high pressure bench reactor (Model no. 4561 Mini Reactor, Parr Instrument Co., Moline, Ill. 61265) equipped with a temperature controller/digital tachometer unit (Model no. 4842, Parr Instrument Co.) and dial pressure gauge. All wetted parts of the reactor were fabricated from type 316 stainless steel. Ordinarily, type 316SS is not the material of choice for inorganic acid systems such as the solution precursors used in this invention, since phosphoric acid can attack stainless steel at elevated temperatures and pressures. However, in the practice of this invention, direct contact (i.e. wetting) of the reactor surfaces was avoided through the use of a Pyrex glass liner. Only the stirrer and thermocouple sheath were immersed in the reactant solutions and no corrosion was observed. In addition, it is assumed that the high nitrate ion concentration in the reactant mixture provided a passivating environment for the type 316SS.

One hundred grams (approximately 100 ml) of the calcium nitrate—sodium hypophosphite solution was placed in the Pyrex liner of the reactor and the intervening space between the glass liner and the reactor vessel was filled with distilled water to the level of the sample. This ensured maximum heat transfer to the sample since the reactor was externally heated by an electric mantle. The approx. 100 ml sample volume left sufficient head space in the reactor to accommodate solution expansion at elevated temperatures. The reactor was sealed by compression of a Teflon gasket. Heating of the reactor was performed at the maximum rate of the controller to a setpoint of 202° C. with constant stirring (500 r.p.m.). The heating profile, as monitored by a thermocouple immersed in the reactant mixture, was as follows:

| REACTOR THERMAL PROFILE | | | | | | | | | |
|---|---|---|---|---|---|---|---|---|---|
| Time(min) | 0 | 5 | 10 | 15 | 20 | 25 | 30 | 35 | 36 |
| Temp. (° C.) (+/−2° C.) | 22 | 49 | 103 | 122 | 145 | 155 | 179 | 197 | 260 (hold) |
| Pressure (psi) | — | — | — | — | — | — | 160 | 210 | 220 |

After holding at 200+/−3° C. for 12 minutes, the temperature rapidly increased to 216° C. with a resultant increase in reactor pressure to approximately 330 psi. This exothermic event quickly subsided as evidenced by the rapid drop in reactor temperature to 208° C. within two minutes as the Parr reactor approached thermal equilibrium via a near-adiabatic process. After 15 minutes at 200° C., the reactor was removed from the heating mantle, quenched in a cold water bath, and opened after the head space was vented to ambient pressure.

A white precipitate was present in the glass liner. The solid was collected by vacuum filtration on a 0.45 micron membrane filter (Millipore, Inc., Bedford, Mass., 01730), washed several times with distilled water, and dried at approximately 55° C. in a forced convection oven. X-ray diffraction of this solid was conducted as described in Example 1.

Figure 13:
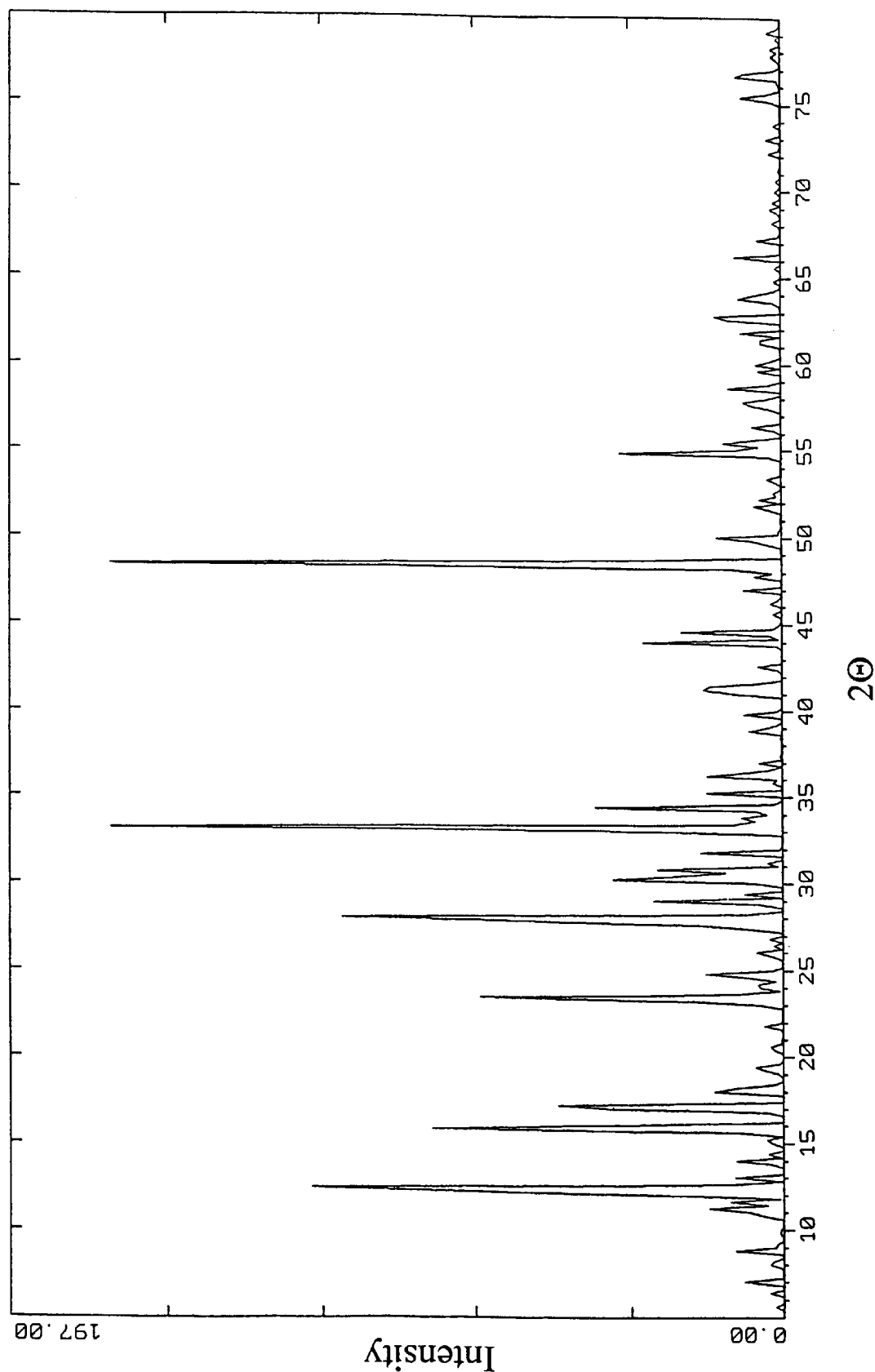
FIG. 13 is an X-ray Diffraction (XRD) plot of HYPR generated calcium phosphate precursor mineral heated to 500° C. for 1 hour. The peak position and relative intensities indicate the presence of an as yet unidentified calcium phosphate crystal phase.

X-Ray diffraction results indicate a unique, unidentifiable diffraction pattern, see FIG. 13.

Example 14

Novel Low Temperature Hydrothermal (HYPR) Calcium Phosphate Powder Preparation Example 13 was repeated except that 40.3 g of 1.0 M NaOH solution was added with rapid stirring to the homogeneous solution of calcium nitrate and sodium hypophosphite instead of the distilled water. This base addition resulted in the formation of a milk white dispersion, presumably due to precipitation of Ca(OH)$_2$.

The sample was hydrothermally processed as described in Example 13 with the temperature setpoint at 207° C. The temperature ramp to 160° C. (25 minutes) was as indicated for Example 13. At 30 minutes into the run, an exotherm occurred causing the temperature of the reaction mixture to rise to a maximum of 221° C. within five minutes with a corresponding pressure increase to 370 psi. At 38 minutes into the experiment, the reactor was quenched to room temperature.

Figure 14:
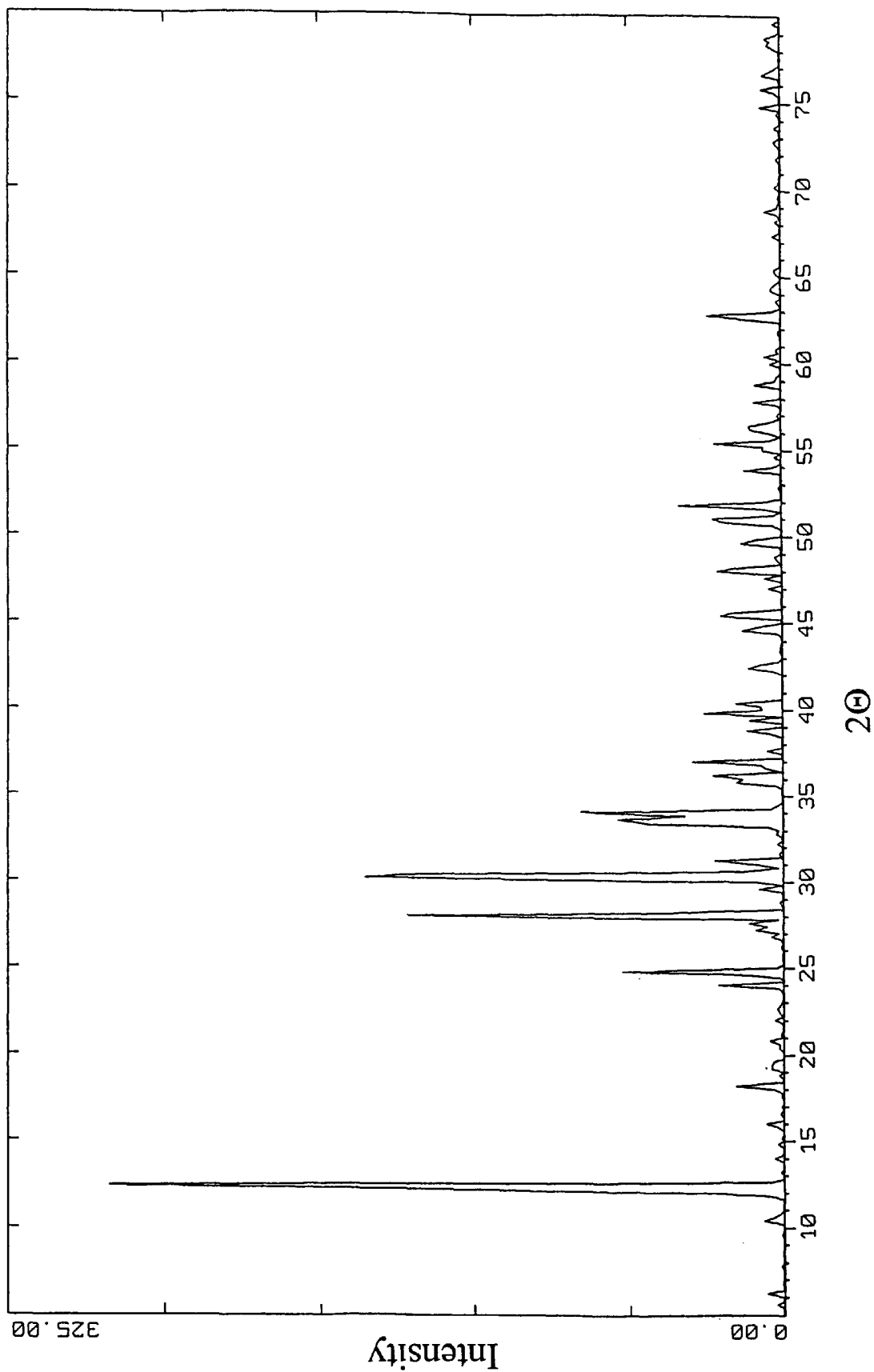
FIG. 14 is an X-ray Diffraction (XRD) plot of HYPR generated calcium phosphate precursor mineral heated to 500° C. for 1 hour. The peak position and relative intensities indicate the presence of an as yet unidentified calcium phosphate crystal phase and minor amounts of HAp.

The reaction product consisted of a small amount of white precipitate. The material was collected as described in Example 13. X-ray diffraction of the dried sample was conducted as described in Example 1. XRD results indicated the solid to be comprised of the same unidentifiable pattern (crystal phase) found in Example 13 and minor amounts of HAp-[$Ca_5(PO_4)_3(OH)$]. (see FIG. 14).

Example 15

Novel Low Temperature Hydrothermal (HYPR) Calcium Phosphate Powder Preparation

A total of 47.0 g of a 50 wt % aqueous solution of calcium nitrate tetrahydrate was diluted with 53.0 g distilled water. Then, 6.00 g calcium hypophosphite salt, $Ca(H_2PO_2)_2$ (Alfa/Aesar reagent #56168, CAS #7789-79-9), equivalent to 23.57 wt % Ca and 111.7 wt % $[PO_4]^{-3}$, was slurried into the $Ca(NO_3)_2$ solution using rapid agitation. An unknown amount of the calcium hypophosphite remained undissolved in the room temperature sample. The solubility behavior of $Ca(H_2PO_2)_2$ in the $Ca(NO_3)_2$ solution at elevated temperatures is unknown. The molar ratio of Ca/phosphate in this system was 1.91.

This sample was hydrothermally processed as described in Example 13 with the temperature setpoint at 212° C. The temperature ramp to 200° C. was as indicated for Example 13. At 39 minutes into the run, an exotherm occurred causing the temperature of the reaction mixture to rise to a maximum of 252° C. within three minutes with a corresponding pressure increase to 640 psi. At 44 minutes into the experiment, the reactor was quenched to room temperature.

Figure 15:
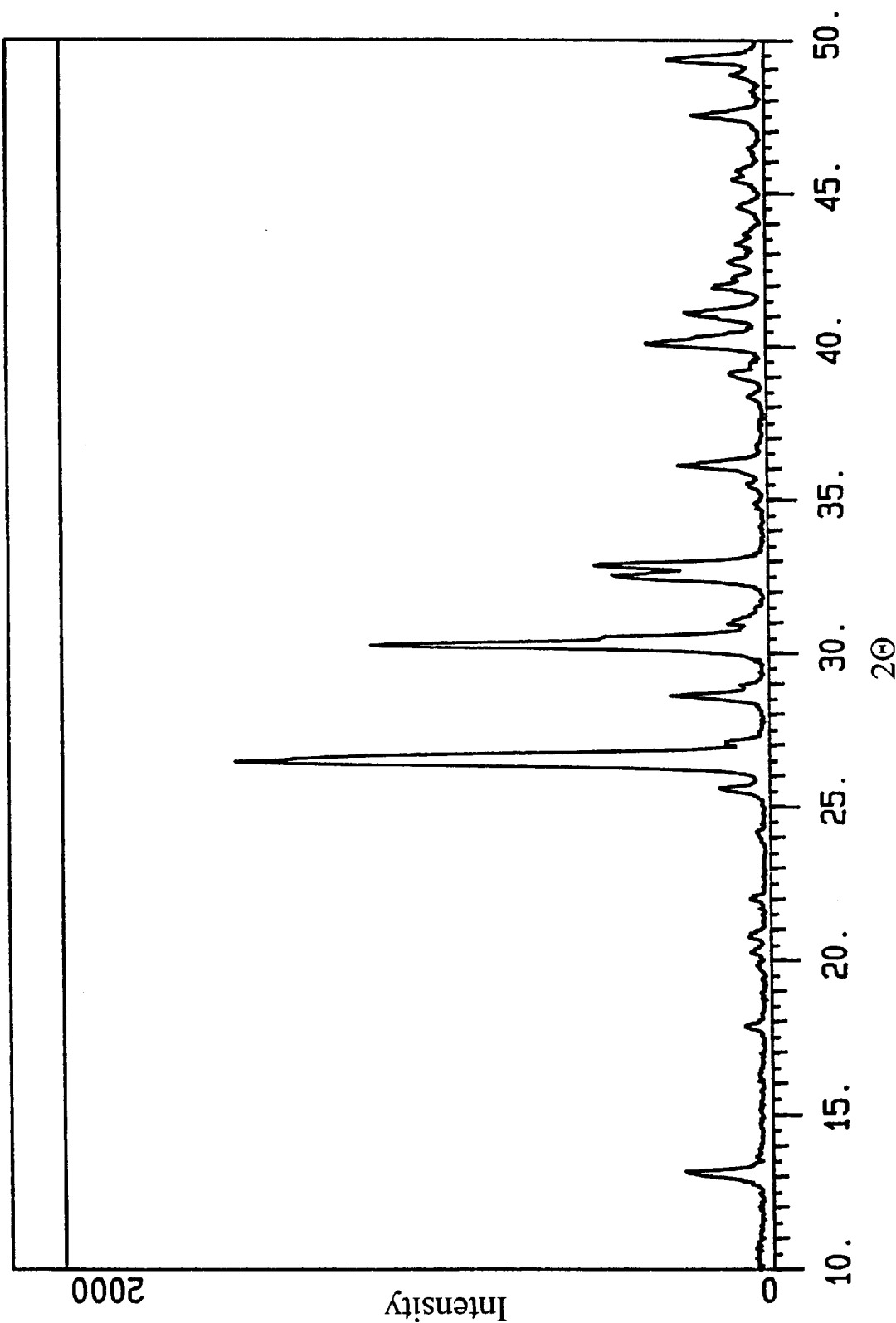
FIG. 15 is an X-ray Diffraction (XRD) plot of HYPR generated calcium phosphate precursor mineral heated to 500° C. for 1 hour. The peak position and relative intensities indicate the presence of the crystal phase monetite [$CaHPO_4$].

The reaction product appeared as a voluminous white precipitate plus some suspended solids. The material was collected as described in Example 13. X-ray diffraction of the dried solid was conducted as described in Example 1. XRD indicated the solid to be monetite, $CaHPO_4$, see FIG. 15. The unique crystal morphology is depicted in the scanning electron micrograph representation in FIG. 2.

Mixtures of the above described RPR and HYPR powders are useful in the formation of self-setting calcium phosphate cements for the repair of dental and orthopaedic defects. The addition of specific components and solubilizing liquids can also be added to form the precursor bone mineral constructs of this invention.

Example 16

Novel Cement Composition

Figure 16:
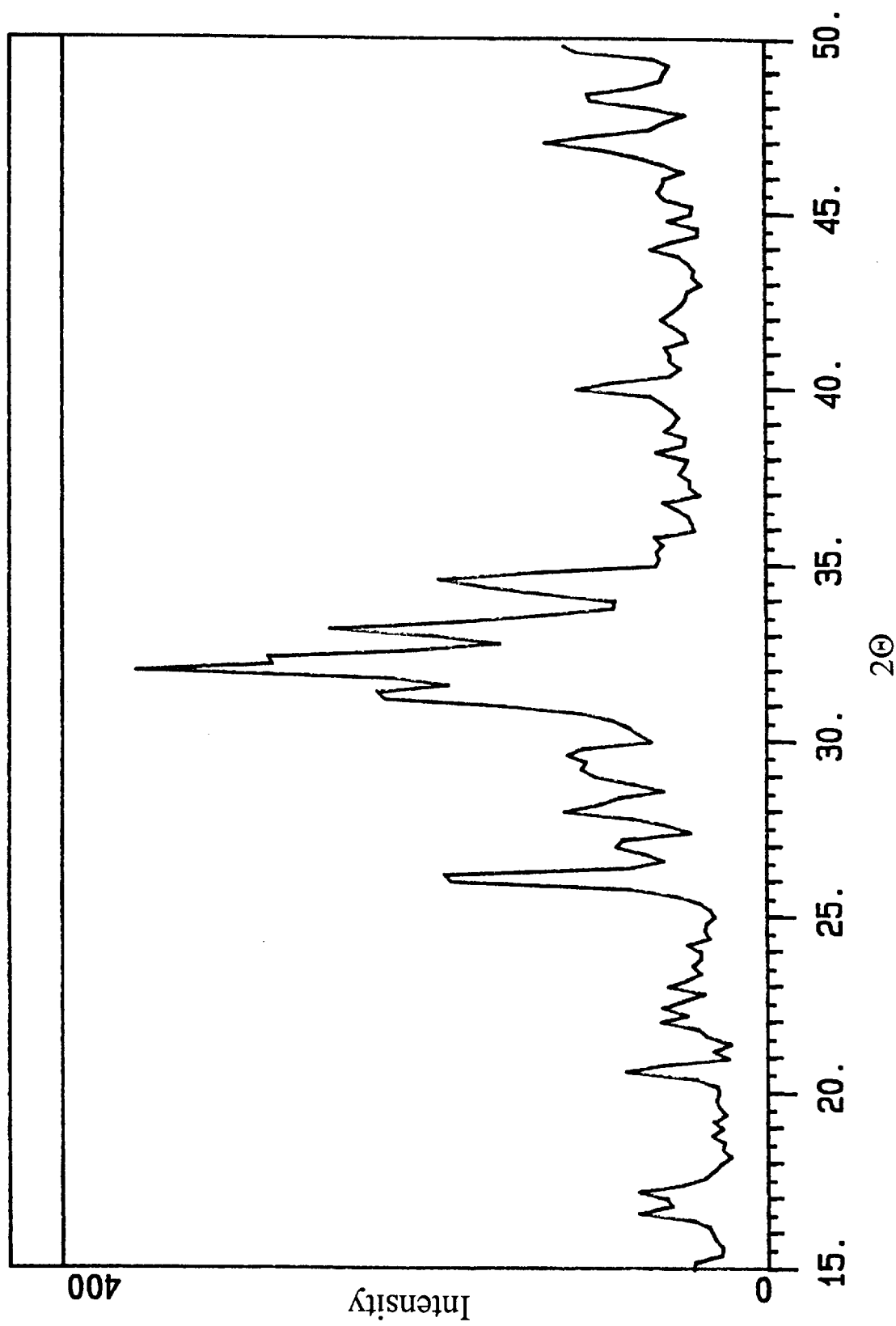
FIG. 16 is an X-ray Diffraction (XRD) plot of RPR and HYPR generated calcium phosphate precursor minerals, heated to 500° C. for 1 hour, and mixed as a cement. The peak position and relative intensities indicate the presence of the crystal phase monetite $CaHPO_4$ mixed with β-TCP+ type-B, carbonated apatite (c-HAp) [β-$Ca_3(PO_4)_2$+$Ca_5$ $(PO_4)_{3-x}(CO_3)_x(OH)$] crystallites.
Figure 17A:
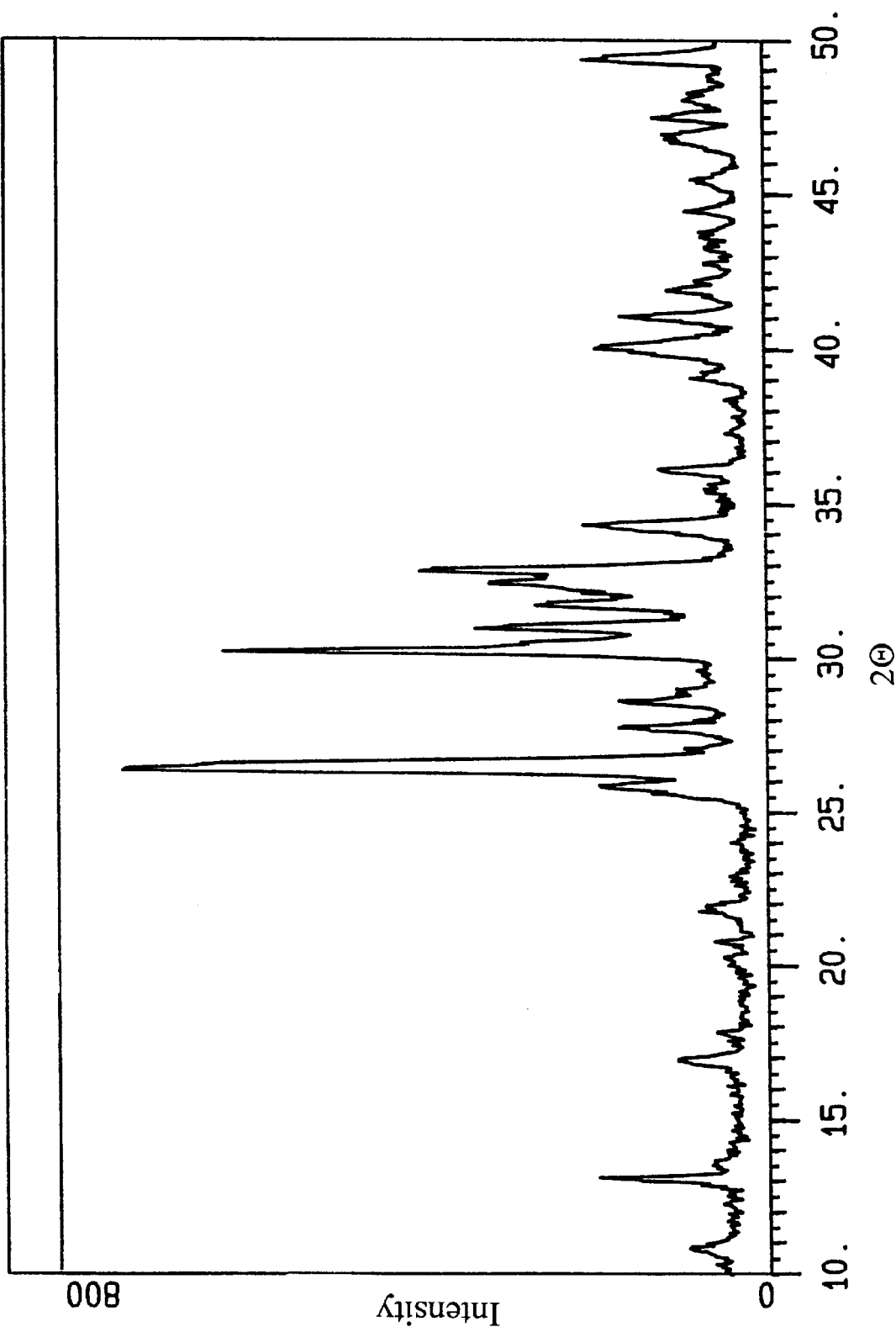
FIG. 17A is an X-ray Diffraction (XRD) plot of RPR and HYPR generated calcium phosphate precursor minerals, heated to 500° C. for 1 hour. The peak position and relative intensities indicate the presence of the crystal phase monetite, $CaHPO_4$, mixed with β-TCP+type-B, carbonated apatite (c-HAp) [β-$Ca_3(PO_4)_2$+$Ca_5(PO_3)_{3-x}$ $(CO_3)_x(OH)$] crystallites.
Figure 17B:
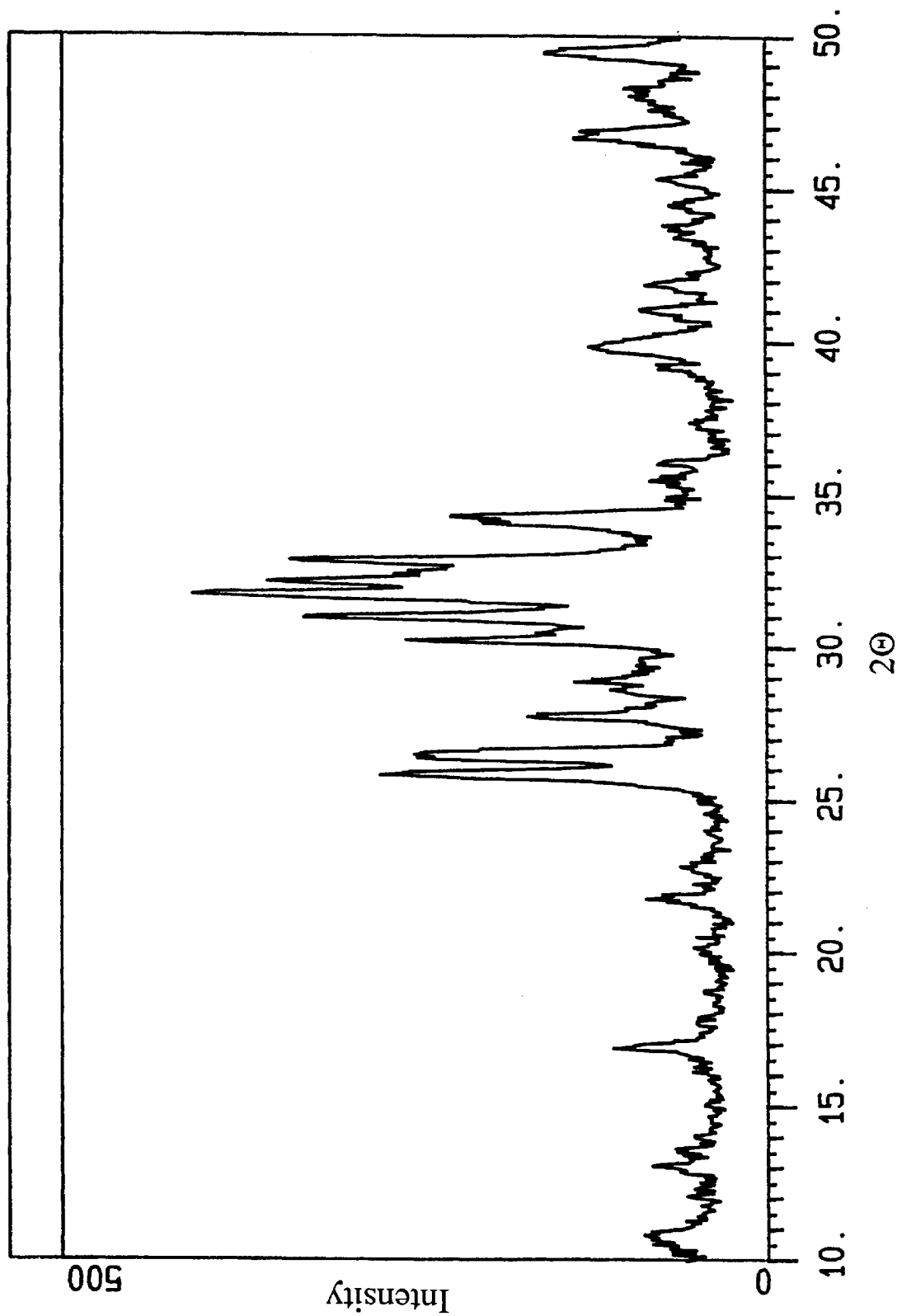
FIG. 17B is an X-ray Diffraction (XRD) plot of RPR and HYPR generated calcium phosphate precursor minerals, heated to 500° C. for 1 hour, and mixed into a cement. The peak position and relative intensities indicate the presence of the crystal phase β-TCP+type-B, carbonated apatite (c-HAp) [β-$Ca_3(PO_4)_2$+$Ca_5(PO_4)_{3-x}$ $(CO_3)_x(OH)$] crystallites.

Approximately 1.4 g of an alkaline solution (7 molar) formed using NaOH and distilled water, was mixed with 1.1 g of HYPR monetite [Example 15] and 1.1 g of RPR β-TCP-HAp($CO_3$) [Example 3] in a glass mortar and pestle for ~45 seconds. After mixing, a smooth paste was formed, which was scooped into a 3 ml polypropylene syringe and sealed for 20 minutes without being disturbed. Room temperature setting was observed after 20 minutes, which was indicated by the use of a 454 gram Gilmore needle. The hardened cement was analyzed by X-ray diffraction which revealed a conversion to primarily type-B, carbonated apatite which is the desired bone mineral precursor phase (see FIG. 16):

| Cement XRD revealed | (Major) | $Ca_5(PO_4)_{3-x}(CO_3)_x(OH)$ |
|---|---|---|
| | (minor) | Whitlockite [β-$Ca_3(PO_4)_2$] |

Example 17

Novel Cement Composition

A stock solution was formed with the approximately 7 M NaOH solution used in Example 1 and 1.0% polyacrylic acid (PAA). PAA is used as a chelating setting additive and wetting agent. The above solution was used with several powder combinations to form setting cements. A 50/50 powder mix of HYPR monetite [Example 15] and RPR β-TCP—HAp($CO_3$) [Example 3], approximately 0.7 g, was mixed with a glass spatula on a glass plate with 0.39 g of the 1% PAA-NaOH solution (powder to liquid ratio=1.73). The cement was extruded through a 3 ml syringe and was set after being left undisturbed for 20 minutes at room temperature (23° C.).

Examples 18–34

| Example | Powder | Liquid | Powder/ Powder/ Liquid ratio (Consistency) | Set Time (min.) Gilmore Needle (454 grams) # = (1200 grams) |
|---|---|---|---|---|
| 18 | HYPR monetite + RPR (Ex. 1) 500° C. | 7M NaOH Alkaline Sol'n | 1/1/1.2 (slightly wet paste) | <20 min (#) |
| 19 | HYPR monetite (Ex. 15) + RPR (Ex. 1) 700° C. | 7M NaOH Alkaline Sol'n | 1/1/1.2 (wet paste) | <20 min (#) |
| 20 | HYPR monetite (Ex. 15) + ~50 μm 45S5# glass | 7M NaOH Alkaline Sol'n | 1/1/1 (sl. wet paste) | 15–18 min |
| 21 | RPR (Ex. 1) 500° C. 'neat' | 7M NaOH Alkaline Sol'n | 1.5/1 (wet paste) | >40 min |
| 22 | RPR (Ex.1) 300° C. + RPR (Ex. 9) 500° C. | 7M NaOH Alkaline Sol'n | 1.7/1 (sl. wet paste) | 40 min |

-continued

| Example | Powder | Liquid | Powder/ Powder/ Liquid ratio (Consistency) | Set Time (min.) Gilmore Needle (454 grams) # = (1200 grams) |
|---|---|---|---|---|
| 23 | HYPR monetite (Ex. 15) + Commercial β-TCP | 7M NaOH Alkaline Sol'n | 1/1/1.4 (v. gritty, wet) | No Set up to 24 hrs. |
| 24 | HYPR monetite (Ex. 15) + RPR (Ex. 2) 500° C. | 7M NaOH Alkaline Sol'n | 1/1/1.4 (slightly wet paste) | 20 min (#) |
| 25 | HYPR monetite (Ex. 15) + RPR (Ex. 2) 500° C. | 7M NaOH Alk. Sol'n + 20% PAA | 1/1/1 (claylike paste) | <30 min sl. set |
| 26 | HYPR monetite (Ex. 15) + RPR (Ex. 2) 500° C. | 7M NaOH Alk. Sol'n + 5% PAA | 1/1/1 (claylike paste) | 35 min. |
| 27 | HYPR monetite (Ex. 15) + RPR (Ex. 11) 500° C. | 7M NaOH Alk. Sol'n + 1% PAA | 1/1/1.2 (slightly dry paste) | 12–15 min |
| 28 | HYPR monetite (Ex. 15) + RPR (Ex. 1) 500° C. | 10 wt % $Ca(H_2PO_2)_2$ (aq) | 1/1/1.2 (very wet paste) | 1 hr 15 min |
| 29 | RPR (Ex. 11) 500° C. 'neat' | 10 wt % $Ca(H_2PO_2)_2$ (aq) | 1.7/1 (very wet paste) | 45 min |
| 30 | RPR (Ex. 11) 500° C. 'neat' | 10 wt % $Ca(H_2PO_2)_2$ (aq) | 2.5/1 (sl. dry paste/putty) | 20 min |
| 31 | RPR (Ex. 11) 500° C. 'neat' | 10 wt % $Ca(H_2PO_2)_2$ + 1 wt % $H_2PO_2$ (aq) | 2.25/1 (very good paste/putty) | 15 min |
| 32 | HYPR monetite (Ex. 15) + RPR (Ex. 11) 500° C. | 3.5M NaOH Alk. Sol'n. | 1/1/1 (good paste/putty) | 35 min. *12 min. |
| 33 | HYPR monetite (Ex. 15) + RPR (Ex. 11) 500° C. | 3.5M NaOH Alk. Sol'n. | 1/3/2 (paste/putty) | 38 min. *15 min. |
| 34 | HYPR monetite (Ex. 15) + RPR (Ex. 11) 500° C. | Saline, EDTA buffered | 1/1/1 (good paste/putty) | 43 min. *20 min. |

*= Set Time at 37° C., 98% Relative Humidity.
HYPR monetite = HYdrothermally PRocessed monetite ($CaHPO_4$).
RPR = Reduction-oxidation Precipitation Reaction.
45S5# glass = {24.5% CaO-24.5% $Na_2O$-6% $P_2O_5$-45% $SiO_2$ (wt %)}.
PAA = Polyacrylic acid.
Commercial β-TCP from Clarkson Chromatography Products, Inc. (S. Williamsport, PA)

. . .

Example 35

Novel Low Temperature Neodymium Phosphate Powder Preparation

Figure 18A:
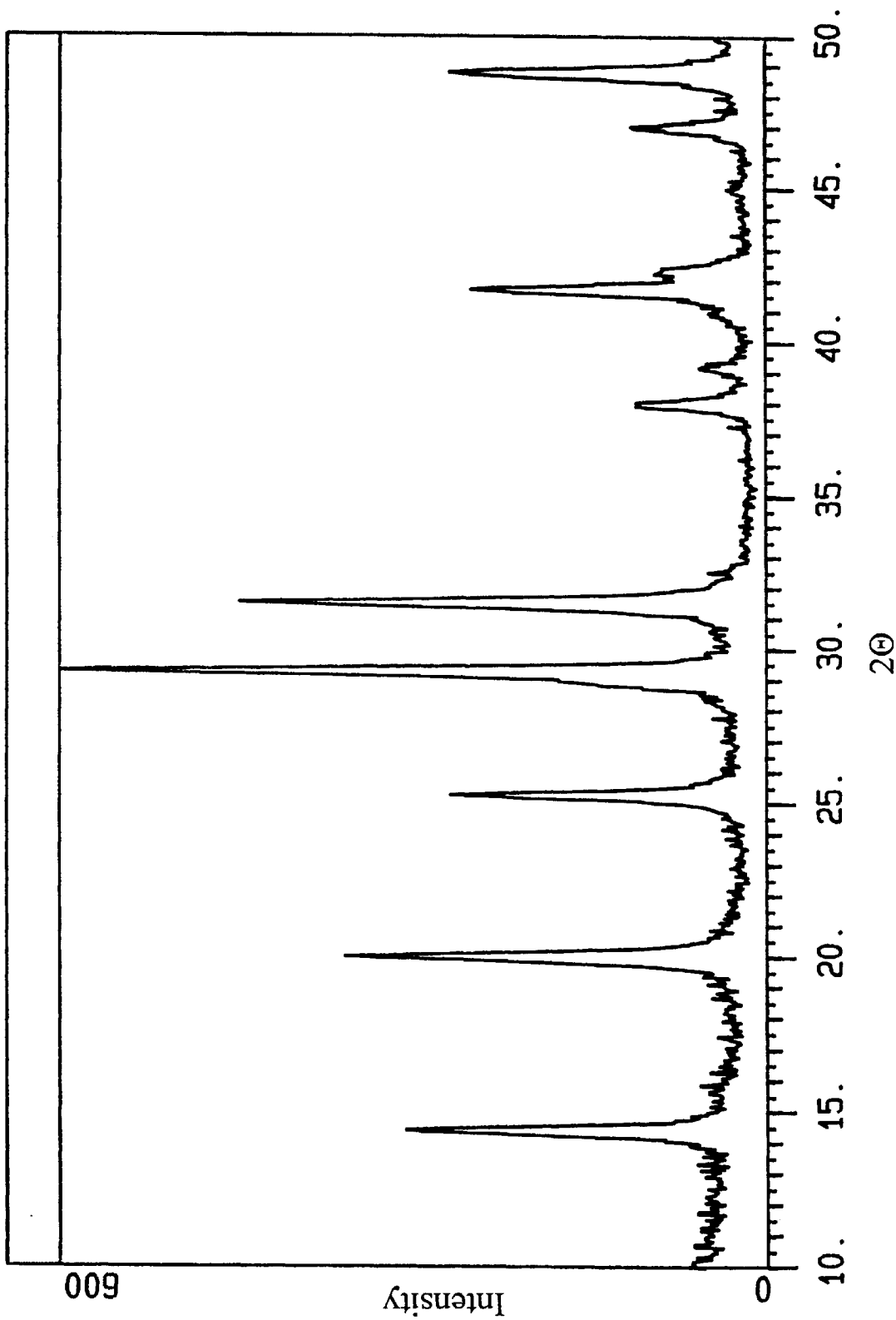
FIG. 18A is an X-ray Diffraction (XRD) plot of RPR generated neodymium phosphate precursor mineral heated to 500° C. for 1 hour. The peak position and relative intensities indicate the presence of the crystal phase neodymium phosphate hydrate [$NdPO_4$·$0.5H_2O$].
Figure 18B:
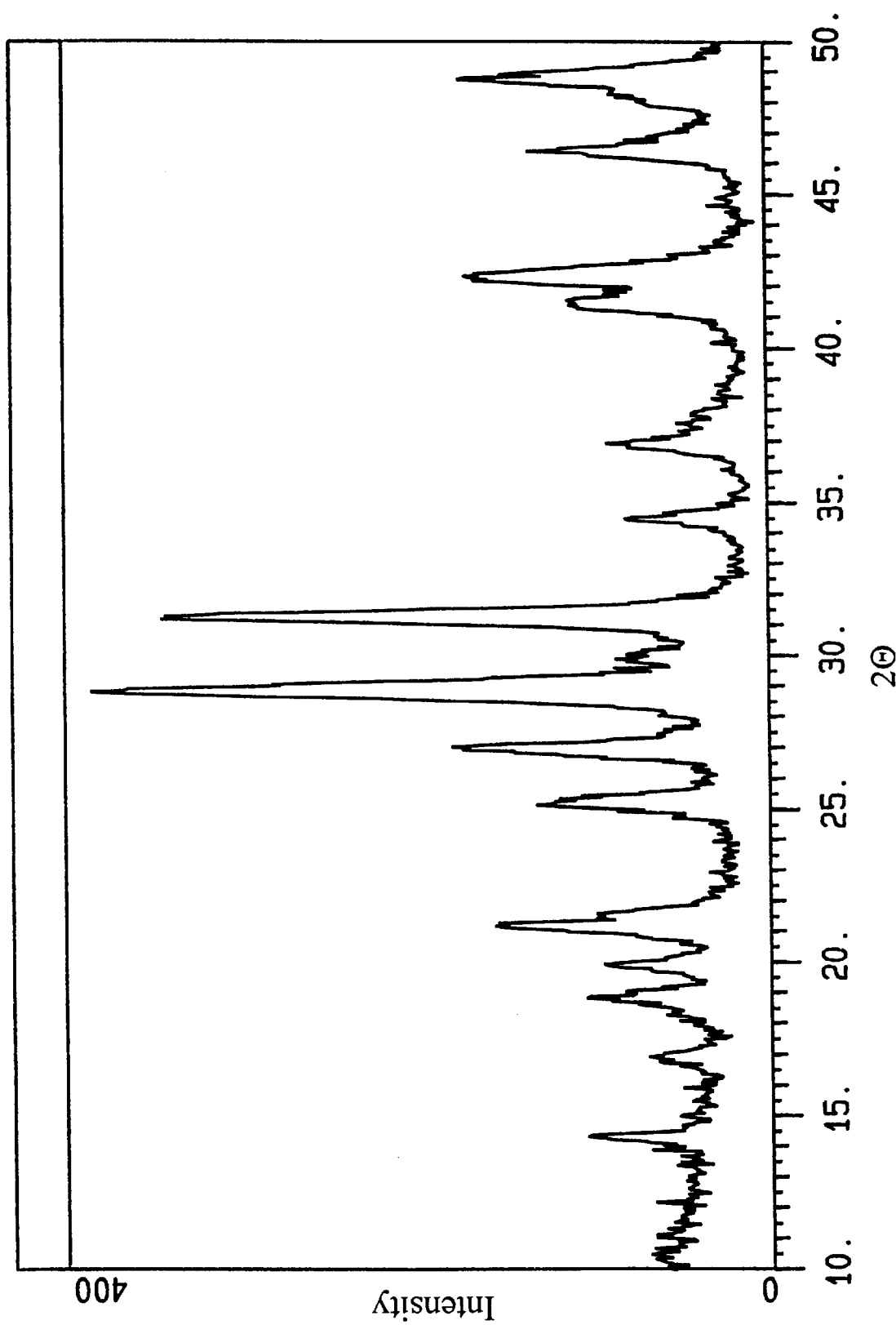
FIG. 18B is an X-ray Diffraction (XRD) plot of RPR generated neodymium phosphate precursor mineral heated to 700° C. for 1 hour. The peak position and relative intensities indicate the presence of the crystal phase Monazite-Nd [$NdPO_4$].

An aqueous solution of 11.04 g of 50 wt. %$H_3PO_2$ was diluted with 5.00 g distilled water to form a clear, colorless solution contained in a 250 ml fluoropolymer resin beaker on a hotplate/magnetic stirrer. Added to this solution was 36.66 g neodymium nitrate hexahydrate salt, $Nd(NO_3)_3$-$6H_2O$ (Alfa/Aesar reagent #12912, CAS #16454-60-7), equivalent to 32.90 wt % Nd. The molar ratio of the Nd/P in this mixture was 1/1 and the equivalent solids level (as $NdPO_4$) was 38 wt %. Endothermic dissolution of the neodymium nitrate hexahydrate salt proceeded with gradual warming of the reaction mixture, eventually forming a clear, homogeneous lavender solution at room temperature. Heating of this solution with constant agitation to approximately 70° C. initiated a vigorous endothermic reaction which resulted in the evolution of $NO_{x(g)}$, rapid temperature increase of the sample to approximately 100° C., and finally, formation of a pasty lavender mass. Heat treatment of the pasty solid and subsequent X-ray diffraction analysis of the fired solid were conducted as described in Example 1. Results are as follows (see FIGS. 18A & B):

| Heated to 500° C., 45 min. | (Major) | Neodymium phosphate hydrate [$NdPO_4$-$0.5H_2O$] |
| Heated to 700° C., 45 min. | (Major) | Monaazite-Nd [$NdPO_4$] |

Example 36

Novel Low Temperature Cerium Phosphate Powder Preparation

Figure 18C:
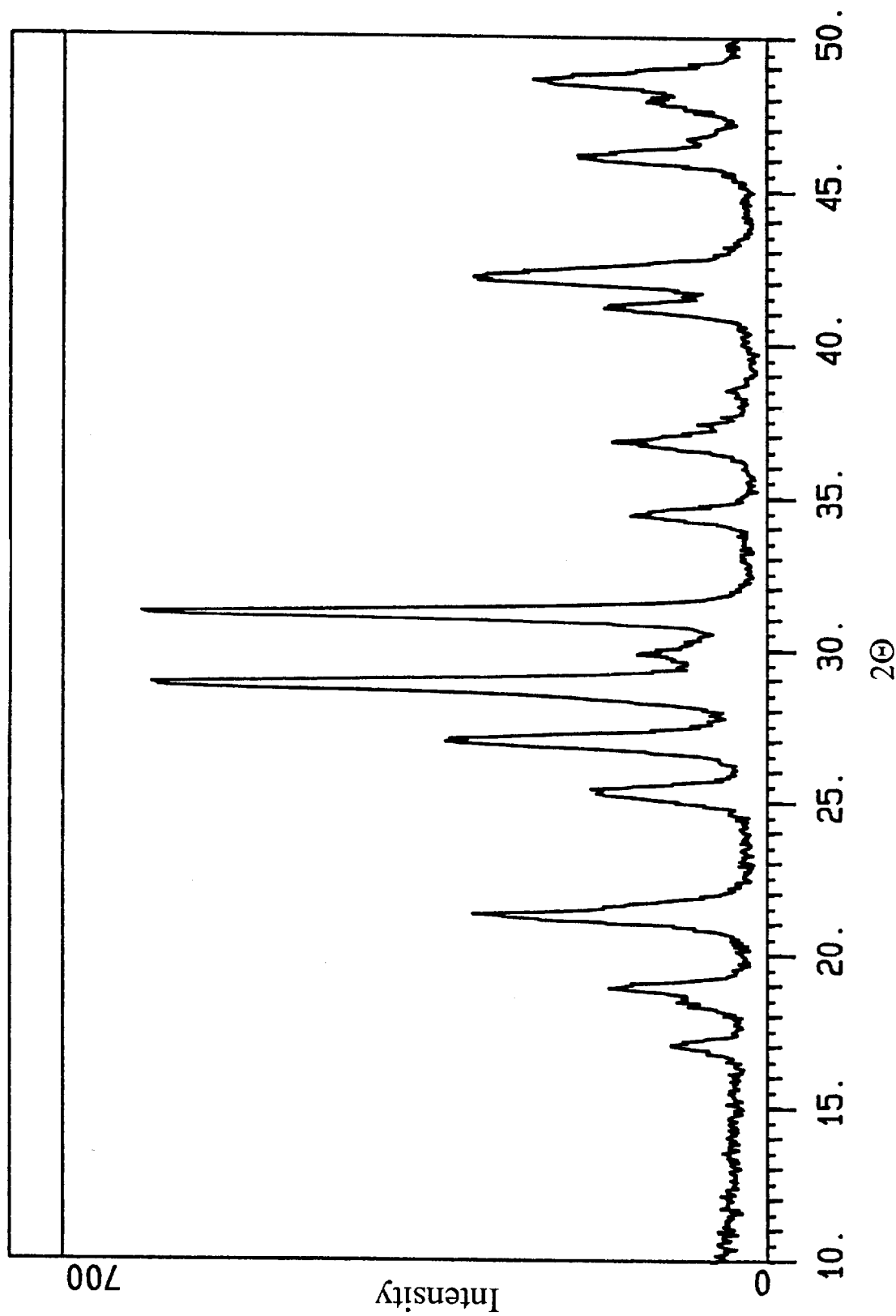
FIG. 18C is an X-ray Diffraction (XRD) plot of RPR generated cerium phosphate precursor mineral heated to 700° C. for 1 hour. The peak position and relative intensities indicate the presence of the crystal phase Monazite-Ce [$CePO_4$].

An aqueous solution of 11.23 g of 50 wt. %$H_3PO_2$ was diluted with 5.00 g distilled water to form a clear, colorless solution contained in a 250 ml fluoropolymer resin beaker on a hotplate/magnetic stirrer. Added to this solution was 36.94 g cerium nitrate hexahydrate salt, $Ce(NO_3)_3$-$6H_2O$ (Johnson-Matthey reagent #11329-36), equivalent to 32.27 wt % Ce. The molar ratio of the Ce/P in this mixture was 1/1 and the equivalent solids level (as $CePO_4$) was 37.6 wt %. Endothermic dissolution of the neodymium nitrate hexahydrate salt proceeded with gradual warming of the reaction mixture, eventually forming a clear, homogeneous colorless solution at room temperature. Heating of this solution with constant agitation to approximately 65° C. initiated a vigorous endothermic reaction which resulted in the evolution of $NO_{x(g)}$, rapid temperature increase of the sample to approximately >100° C., and finally, formation of a pasty light grey mass. Heat treatment of the pasty solid and subsequent X-ray diffraction analysis of the fired solid were conducted as described in Example 1. Results are as follows (see FIG. 18C):

| | | |
|---|---|---|
| Heated to 700° C., 45 min. | (Major) | Monazite-Ce [CePO$_4$] |

Example 37

Novel Low Temperature Yttrium Phosphate Powder Preparation

Figure 18D:
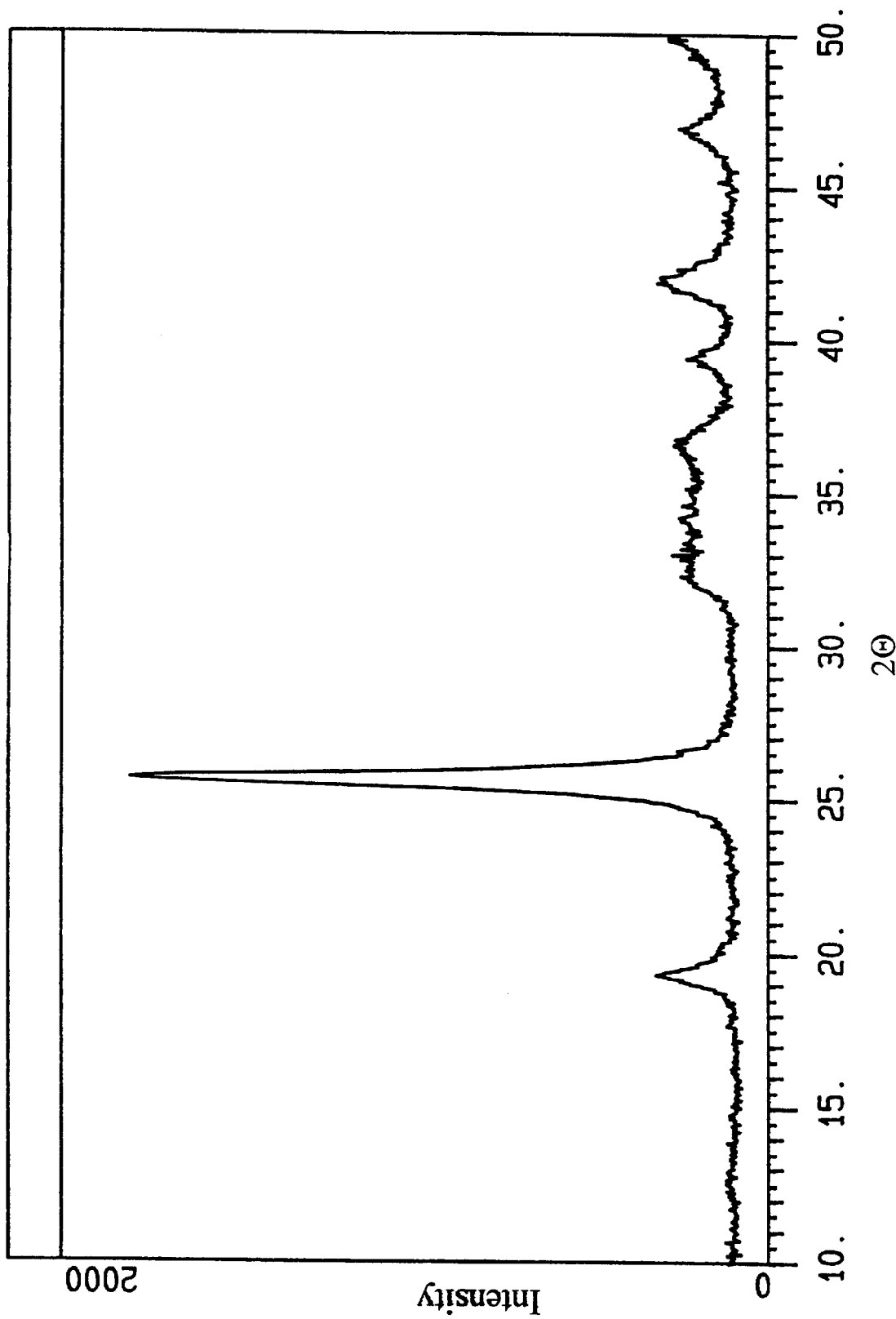
FIG. 18D is an X-ray Diffraction (XRD) plot of RPR generated yttrium phosphate precursor mineral heated to 700° C. for 1 hour. The peak position and relative intensities indicate the presence of the crystal phase Xenotime [$YPO_4$].

An aqueous solution of 14.36 g of 50 wt. %H$_3$PO$_2$ was diluted with 5.00 g distilled water to form a clear, colorless solution contained in a 250 ml fluoropolymer resin beaker on a hotplate/magnetic stirrer. Added to this solution was 41.66 g yttrium nitrate hexahydrate salt, Y(NO$_3$)$_3$·6H$_2$O (Alfa/Aesar reagent #12898, CAS #13494-98-9), equivalent to 23.21 wt % Y. The molar ratio of the Y/P in this mixture was 1/1 and the equivalent solids level (as YPO$_4$) was 32.8 wt %. Endothermic dissolution of the yttrium nitrate hexahydrate salt proceeded with gradual warming of the reaction mixture, eventually forming a clear, homogeneous colorless solution at room temperature. Heating of this solution with constant agitation to approximately 75° C. initiated a vigorous endothermic reaction which resulted in the evolution of $NO_{x(g)}$, rapid temperature increase of the sample to approximately >100° C., and finally, formation of a pasty white mass. Heat treatment of the pasty solid and subsequent X-ray diffraction analysis of the fired solid were conducted as described in Example 1. Results are as follows (see FIG. 18D):

| | | |
|---|---|---|
| Heated to 700° C., 45 min. | (Major) | Xenotime [YPO$_4$] |

Example 38

A wide variety of minerals can be made in accordance with the the present invention. In the following two tables, oxidizing and reducing agents are listed. Any of the listed oxidants can be reacted with any of the listed reducing agents and, indeed, blends of each may be employed. Appropriate stoichiometry will be employed such that the aforementioned reaction is caused to proceed. Also specified are possible additives and fillers to the reactions. The expected products are given as are some of the expected fields of application for the products. All of the following are expected generally to follow the methodology of some or all of the foregoing Examples.

| Oxidizing Agents | Reducing Agents | Additives | Product(s) |
|---|---|---|---|
| Compounds of the form XNO$_3$, where X= H, Li, Na, K, Rb, Cs, Cu, Ag, and Hg. Compounds of the form X(NO$_3$)$_2$, where X = Be, Mg, Ca, Sr. Ba, Cr, Mn, Fe, Co, Ni, Cu, Zn, Rh, Pd, Cd, Sn, Hg, and Pb | Oxoacids of Group 5B, 6B, and 7B, (where 5B includes N, P, and As; 6B includes S, Se, and Te; 7B includes Cl, Br, and I). Phosphorous oxoacid compounds: Hypophosphite (H$_3$PO$_2$); Hypophosphoric acid (H$_4$P$_2$O$_6$); Isohypophosphoric acid (H$_4$P$_2$O$_6$); Phosphonic acid or phosphorus acid (H$_3$PO$_3$); Diphosphonic acid (H$_4$P$_2$O$_5$); Phosphinic acid or hypophosphorus acid (H$_3$PO$_2$). | Al$_2$O$_3$, ZrO$_2$, TiO$_2$, SiO$_2$, Ca(OH)$_2$, DCPD, DCPA, HAp, TCP, TTCP, MCMP, ZrSiO$_4$, W-metal, Fe metal, Ti metal, Carbon black, C-fiber or flake, CaF$_2$, NaF, carbides, nitrides, glass fibers, glass particulate, glass-ceramics, alumina fibers, ceramic fibers, bioactive ceramic fibers and particulates, polyacrylic acid, polyvinyl alcohol, polymethyl-methacrylate, polycarbonate, and other stable polymeric compounds. Acetates, formates, lactates, simple carboxylates, and simple sugars. | XY(PO$_4$), XY(SO$_4$), XY(PO$_4$)(SO$_4$), WXYZ(PO$_4$)(SO$_4$)(CO$_3$), WXYZ(PO$_4$)(SO$_4$)(CO$_3$)(F, Cl, Br, I), WXYZ(PO$_4$)(SO$_4$) (CO$_3$)(F, Cl, Br, I)(OCl, OF, OBr, OI), in the form of fiber, flake, whisker, granule, coatings, agglomerates and fine powders. |
| Compounds of the form X(NO$_3$)$_3$, or XO(NO$_3$), where X = Al, Cr, Mn, Fe, Co, Ni, Ga, As, Y, Nb, Rh, In, La, Tl, Bi, Ac, Ce, Pr, Nd, Sm, Eu, Gd, Tb, Dy, Ho, Er, Tm, Yb, Lu, U, and Pu Compounds of the form X(NO$_3$)$_4$ or XO(NO$_3$)$_2$, where X = Mn, Sn, Pd, Zr, Pb, Ce, Pr, Th, Th, Pa, U and Pu. Halogen oxoacids: perhalic acid (HOClO$_3$, HOBrO$_3$, HOIO$_3$); halic acid (HOClO$_2$, HOBrO$_2$, HOIO$_2$); halous acid (HOClO, HOBrO, HOIO) | Sulfur oxoacid compounds: Thiosulfuric acid (H$_2$S$_2$O$_3$); Dithionic acid (H$_2$S$_2$O$_6$); Polythionic acid (H$_2$S$_{n+2}$O$_6$); Sulfurous acid (H$_2$SO$_3$); Disulfurous acid (H$_2$S$_2$O$_5$); Dithionous acid (H$_2$S$_2$O$_4$). | | |

The minerals prepared above may be used in a wide variety of applications. Exemplary of these applications are in pigments, phosphors, fluorescing agents, paint additives, synthetic gems, chromatography media, gas scrubber media, filtration media, bioseparation media, zeolites, catalysts, catalytic supports, ceramics, glasses, glass-ceramics, cements, electronic ceramics, piezoelectric ceramics, bioceramics, roofing granules, protective coatings, barnacle retardant coating, waste solidification, nuclear waste solidification, abrasives, polishing agents, polishing pastes, radiopharmaceuticals, medical imaging and diagnostics agents, drug delivery, excipients, tabletting excipients, bioactive dental and orthopaedic materials and bioactive coatings, composite fillers, composite additives, viscosity adjustment additives, paper finishing additives, optical coatings, glass coatings, optical filters, fertilizers, soil nutrient(s) additives.

What is claimed is:

1. A substantially homogeneous calcium phosphate salt that is an oxidation-reduction product formed by:
   preparing an aqueous solution comprising:
      a metal cation which is calcium;
      at least one oxidizing agent; and
      at least one precursor anion oxidizable by said oxidizing agent to form a phosphate; and
   heating said solution under conditions of temperature and pressure effective to initiate an oxidation-reduction reaction between said oxidizing agent and the precursor anion; said reaction evolving at least one gaseous product; and giving rise to said phosphates said metal phosphate, salt precipitating from said solution, and comprised of individual crystallites having a crystal size of about 1 micron or below.

2. The calcium phosphate salt of claim 1 having substantially uniform morphology.

3. The calcium phosphate salt of claim 1 having a non-stoichiometric composition.

4. Substantially homogeneous, bioactive and biocompatible calcium phosphate that is an oxidation-reduction product produced by:
   preparing an aqueous solution of a phosphorus oxoacid and a calcium nitrate;
   heating said solution to a temperature of about 250° C. or below under conditions of temperature and pressure effective to initiate an oxidation-reduction reaction between the oxoacid and the calcium nitrate; said reaction evolving nitrogen oxide gas; and
   said calcium phosphate precipitating from said solution wherein said calcium phosphate is comprised of individual crystallites have a crystal size of about 1 $\mu$m or below.

5. The calcium phosphate produced in accordance with claim 4 being further derived by heating to a temperature above about 100° C.

6. The calcium phosphate produced in accordance with claim 5 wherein said heating is to a temperature below about 700° C.

7. The bioactive and biocompatible calcium phosphate of claim 4 wherein said phosphorus oxoacid is hypophosphorus acid.

8. A bioactive cement for the repair of osseous defects comprising the bioactive and biocompatible calcium phosphate of claim 4.

9. The bioactive and biocompatible calcium phosphate of claim 4 admixed with a pharmaceutically acceptable carrier or diluent.

10. The bioactive and biocompatible calcium phosphate of claim 4 admixed with a polymerizable material.

11. An alkaline earth phosphate salt of an oxidation-reduction product formed by:
    preparing an aqueous solution comprising
       an alkaline earth cation;
       at least one oxidizing agent; and
       at least one precursor anion oxidizable by said oxidizing agent to form a
       phosphate; and
    heating said solution under conditions of temperature and pressure effective to initiate an oxidation-reduction reaction between said oxidizing agent and the precursor anion, said reaction evolving at least one gaseous product; and giving rise to said phosphate, said alkaline earth metal phosphate salt precipitating from said solution wherein said alkaline earth metal phosphate salt is substantially homogeneous and has a substantially fine crystal size of about 1 $\mu$m or below, wherein said alkaline earth metal is calcium.

12. The alkaline earth metal phosphate salt of claim 11 having a non-stoichiometric composition.

* * * * *